United States Patent
Fan et al.

(10) Patent No.: US 11,690,756 B2
(45) Date of Patent: *Jul. 4, 2023

(54) POLYMERS, THERMOCHROMIC AGENTS, AND/OR HYDROGEL COMPOSITIONS AND APPARATUS, INCLUDING PRODUCTS EMBODYING THE SAME, AND METHODS AND PROCESSES FOR MAKING SAME

(71) Applicants: Shanghai Chuangshi Medical Technology (Group) Co., Ltd., Shanghai (CN); Biofreeze IP Holdings, LLC, Akron, OH (US)

(72) Inventors: Litao Fan, Shanghai (CN); Yong You, Shanghai (CN); Yunguang Pan, Shanghai (CN); Dongjia He, Shanghai (CN); Rocco Mango, Avon Lake, OH (US)

(73) Assignees: BIOFREEZE IP HOLDINGS, LLC, Parsippany, NJ (US); SHANGHAI CHUANGSHI MEDICAL TECHNOLOGY (GROUP) CO., LTD., Shanghai (CN)

( * ) Notice: Subject to any disclaimer, the term of this patent is extended or adjusted under 35 U.S.C. 154(b) by 839 days.

This patent is subject to a terminal disclaimer.

(21) Appl. No.: 16/425,557

(22) Filed: May 29, 2019

(65) Prior Publication Data

US 2019/0307602 A1 Oct. 10, 2019

Related U.S. Application Data

(60) Division of application No. 15/986,790, filed on May 22, 2018, now Pat. No. 10,492,943, which is a
(Continued)

(51) Int. Cl.
*A61F 7/02* (2006.01)
*A61F 7/00* (2006.01)
(Continued)

(52) U.S. Cl.
CPC ............... *A61F 7/02* (2013.01); *C08K 3/30* (2013.01); *C08K 5/0041* (2013.01); *C08K 5/14* (2013.01);
(Continued)

(58) Field of Classification Search
CPC combination set(s) only.
See application file for complete search history.

(56) References Cited

U.S. PATENT DOCUMENTS

| 264,814 | A | 9/1882 | Wood |
| D45,122 | S | 1/1914 | Meinecke |

(Continued)

FOREIGN PATENT DOCUMENTS

| CA | 146063 S | 1/2013 |
| CA | 144326 S | 3/2013 |

(Continued)

OTHER PUBLICATIONS

Entire prosecution history of U.S. Appl. No. 10/672,132.
(Continued)

*Primary Examiner* — Joseph A Stoklosa
*Assistant Examiner* — Adam J Avigan
(74) *Attorney, Agent, or Firm* — Pequignot + Myers; Matthew A. Pequignot

(57) ABSTRACT

Polymers, hydrogels, and thermochromic agents, including products embodying them, methods of using them, and processes for making them. In certain embodiments, temperature therapy packs which utilize thermochromic agents integrated into solid, semi-solid, or liquid hydrogels. In preferred (but optional) embodiments, the thermochromic agents are integrated into the composition used as the temperature exchange material of the therapy pack. In certain other embodiments, methods of using the thermochromic integrated temperature exchange materials, or
(Continued)

processes for manufacturing such thermochromic integrated temperature exchange materials and/or methods or processes for manufacturing or using thermal packs embodying such materials. In certain particularly preferred embodiments, novel polymer compositions and/or processes for making polymers, which improve product durability or longevity and/or which improve use cycles or usage times.

13 Claims, 7 Drawing Sheets

Related U.S. Application Data continuation of application No. PCT/CN2018/077916, filed on Mar. 2, 2018.

(51) Int. Cl.

| | |
|---|---|
| C08L 33/26 | (2006.01) |
| C08L 1/12 | (2006.01) |
| C08L 1/14 | (2006.01) |
| C08L 1/28 | (2006.01) |
| C08L 3/02 | (2006.01) |
| C08L 3/12 | (2006.01) |
| C08L 5/04 | (2006.01) |
| C08L 5/06 | (2006.01) |
| C08L 5/12 | (2006.01) |
| C08K 5/00 | (2006.01) |
| C08K 5/14 | (2006.01) |
| C08K 3/30 | (2006.01) |
| C08L 33/02 | (2006.01) |
| G01K 11/16 | (2021.01) |

(52) U.S. Cl.
CPC ...... *C08L 1/12* (2013.01); *C08L 1/14* (2013.01); *C08L 1/284* (2013.01); *C08L 3/02* (2013.01); *C08L 3/12* (2013.01); *C08L 5/04* (2013.01); *C08L 5/06* (2013.01); *C08L 5/12* (2013.01); *C08L 33/02* (2013.01); *C08L 33/26* (2013.01); *A61F 2007/0095* (2013.01); *A61F 2007/0214* (2013.01); *A61F 2007/0219* (2013.01); *C08K 2003/3054* (2013.01); *G01K 11/16* (2013.01)

(56) References Cited

U.S. PATENT DOCUMENTS

| | | |
|---|---|---|
| 1,690,405 A | 11/1928 | Du Rocher |
| 1,924,315 A | 8/1933 | Hemphill et al. |
| 2,038,275 A | 4/1936 | Fogg |
| D111,793 S | 10/1938 | Myers |
| D164,087 S | 7/1951 | Atkin |
| 2,932,052 A | 4/1960 | Morse |
| 2,955,331 A | 10/1960 | Nelson |
| 3,164,151 A | 1/1965 | Vere |
| D204,884 S | 5/1966 | Waddington |
| 3,301,254 A | 1/1967 | Erich |
| 3,382,511 A | 5/1968 | Brooks |
| 3,545,230 A | 12/1970 | Morse |
| 3,561,435 A | 2/1971 | Nicholson |
| D223,701 S | 5/1972 | Lausch |
| 3,736,769 A | 6/1973 | Petersen |
| 3,768,485 A | 10/1973 | Linick |
| 3,804,077 A | 4/1974 | Williams |
| D232,995 S | 10/1974 | Molzen |
| 3,885,403 A | 5/1975 | Spencer |
| D242,958 S | 1/1977 | Manschot et al. |
| D243,121 S | 1/1977 | Ralston, Jr. et al. |
| D243,715 S | 3/1977 | Trimnell |
| D245,119 S | 7/1977 | Harris |
| 4,122,847 A | 10/1978 | Craig |
| D251,258 S | 3/1979 | Power |
| D251,576 S | 4/1979 | Geenen-Megens |
| D258,532 S | 3/1981 | Wagner |
| 4,316,287 A | 2/1982 | Rule |
| D265,704 S | 8/1982 | Yamamoto et al. |
| 4,462,224 A * | 7/1984 | Dunshee .............. A61F 7/106 62/530 |
| 4,470,417 A | 9/1984 | Gruber |
| D278,363 S | 4/1985 | Schenkel et al. |
| 4,530,220 A | 7/1985 | Nambu et al. |
| 4,559,047 A | 12/1985 | Kapralis et al. |
| 4,580,547 A | 4/1986 | Kapralis et al. |
| 4,585,797 A | 4/1986 | Cioca |
| 4,614,189 A | 9/1986 | MacKenzie |
| 4,645,498 A | 2/1987 | Kosak |
| 4,668,564 A | 5/1987 | Orchard |
| D293,004 S | 12/1987 | Emms |
| D293,829 S | 1/1988 | Johnston |
| 4,727,869 A | 3/1988 | Leonardi |
| D296,838 S | 7/1988 | Diaz |
| D296,930 S | 7/1988 | Carabelli |
| D300,645 S | 4/1989 | Bowden |
| D301,280 S | 5/1989 | Craig et al. |
| D302,213 S | 7/1989 | Motazedi |
| 4,917,112 A | 4/1990 | Kalt |
| D308,787 S | 6/1990 | Youngblood |
| D312,558 S | 12/1990 | Ilsen et al. |
| D318,075 S | 7/1991 | Capper et al. |
| 5,050,595 A | 9/1991 | Krafft |
| D320,457 S | 10/1991 | Dickinson |
| D324,915 S | 3/1992 | Wastchak |
| D325,089 S | 3/1992 | Shaw |
| D326,222 S | 5/1992 | McAtarian |
| D327,329 S | 6/1992 | Hubbard et al. |
| D327,330 S | 6/1992 | Noble |
| 5,129,391 A | 7/1992 | Brodsky et al. |
| D328,792 S | 8/1992 | Salmon et al. |
| D329,497 S | 9/1992 | Pryor |
| D330,427 S | 10/1992 | Meijer |
| 5,163,425 A * | 11/1992 | Nambu ................ A42B 1/008 607/114 |
| D332,310 S | 1/1993 | Ahlen |
| 5,179,944 A | 1/1993 | McSymytz |
| 5,190,033 A | 3/1993 | Johnson |
| D336,339 S | 6/1993 | Pryor |
| 5,219,625 A | 6/1993 | Matsunami et al. |
| D341,022 S | 11/1993 | Zona |
| D341,284 S | 11/1993 | Martin |
| 5,274,865 A | 1/1994 | Takehashi |
| D343,903 S | 2/1994 | Perteet |
| 5,300,103 A | 4/1994 | Stempel et al. |
| 5,300,105 A | 4/1994 | Owens |
| 5,304,215 A | 4/1994 | MacWhinnie et al. |
| 5,314,005 A | 5/1994 | Dobry |
| D348,174 S | 6/1994 | Genis |
| D349,018 S | 7/1994 | Kaiser |
| D351,472 S | 10/1994 | Mason et al. |
| D352,633 S | 11/1994 | Berggren |
| D353,892 S | 12/1994 | Shaw et al. |
| 5,375,278 A | 12/1994 | VanWinkle et al. |
| D354,138 S | 1/1995 | Kelly |
| D355,457 S | 2/1995 | Miller |
| D356,329 S | 3/1995 | Frilot |
| D357,747 S | 4/1995 | Kelly |
| 5,409,500 A | 4/1995 | Dyrek |
| D360,920 S | 8/1995 | Lessard |
| D363,670 S | 10/1995 | Sullivan |
| D369,218 S | 4/1996 | Vandenbelt |
| 5,545,197 A | 8/1996 | Bowen |
| 5,628,772 A | 5/1997 | Russell |
| D383,213 S | 9/1997 | Ingram |
| D383,546 S | 9/1997 | Amis et al. |
| D383,547 S | 9/1997 | Mason et al. |
| D383,848 S | 9/1997 | Mason et al. |
| D384,703 S | 10/1997 | Chuang |
| D387,506 S | 12/1997 | Kosh |
| 5,707,645 A | 1/1998 | Wierson |
| D390,057 S | 2/1998 | Gower |
| D392,742 S | 3/1998 | Clark |
| D392,787 S | 3/1998 | Barratt |

(56) References Cited

U.S. PATENT DOCUMENTS

| | | | |
|---|---|---|---|
| 5,755,110 A * | 5/1998 | Silvas | A41D 13/0053 |
| | | | 2/458 |
| 5,800,491 A | 9/1998 | Kolen et al. | |
| D401,317 S | 11/1998 | Gillies | |
| D402,147 S | 12/1998 | Scarborough | |
| 5,842,475 A | 12/1998 | Duback et al. | |
| D403,774 S | 1/1999 | Laughlin et al. | |
| D406,350 S | 3/1999 | Cutler | |
| D407,823 S | 4/1999 | Davis et al. | |
| D407,939 S | 4/1999 | Bear | |
| 5,895,656 A | 4/1999 | Hirshowitz et al. | |
| 5,897,580 A | 4/1999 | Silver | |
| D410,090 S | 5/1999 | Podd | |
| D410,165 S | 5/1999 | Bear | |
| D410,167 S | 5/1999 | Bear | |
| D410,749 S | 6/1999 | Podd | |
| D410,750 S | 6/1999 | Podd | |
| D411,624 S | 6/1999 | Podd | |
| 5,925,072 A | 7/1999 | Cramer et al. | |
| 5,978,962 A | 11/1999 | Hamowy | |
| 5,984,953 A | 11/1999 | Sabin et al. | |
| D420,178 S | 2/2000 | Bionde et al. | |
| D426,308 S | 6/2000 | Negron | |
| 6,080,121 A | 6/2000 | Madow et al. | |
| 6,083,254 A | 7/2000 | Evans | |
| D429,818 S | 8/2000 | Lamping et al. | |
| 6,099,555 A | 8/2000 | Sabin | |
| D431,269 S | 9/2000 | Soderstrom | |
| D433,757 S | 11/2000 | Jordan | |
| D434,506 S | 11/2000 | Jordan | |
| 6,146,413 A | 11/2000 | Harman | |
| 6,152,892 A | 11/2000 | Masini | |
| D436,019 S | 1/2001 | Thomas | |
| D436,179 S | 1/2001 | Small | |
| D436,525 S | 1/2001 | Lin | |
| D438,307 S | 2/2001 | Scheppke | |
| D442,078 S | 5/2001 | Fuquen | |
| D442,278 S | 5/2001 | Rury | |
| D442,285 S | 5/2001 | Perry | |
| 6,226,820 B1 | 5/2001 | Navarro | |
| 6,241,711 B1 | 6/2001 | Weissberg et al. | |
| D446,927 S | 8/2001 | Rothschild | |
| D448,850 S | 10/2001 | Fabricant | |
| 6,320,094 B1 | 11/2001 | Arnold et al. | |
| D453,223 S | 1/2002 | Sherman | |
| 6,336,220 B1 | 1/2002 | Sacks et al. | |
| D453,541 S | 2/2002 | Steele et al. | |
| 6,361,553 B1 | 3/2002 | Bowen | |
| D459,986 S | 7/2002 | Yourist | |
| D460,914 S | 7/2002 | Yourist | |
| 6,420,623 B2 | 7/2002 | Augustine et al. | |
| D461,903 S | 8/2002 | Garcia | |
| D466,610 S | 12/2002 | Ashton et al. | |
| 6,524,331 B1 | 2/2003 | Kohout et al. | |
| D473,940 S | 4/2003 | Hantke et al. | |
| D473,947 S | 4/2003 | Jacobson | |
| D476,080 S | 6/2003 | Hantke et al. | |
| D477,086 S | 7/2003 | Tsuruda et al. | |
| 6,610,084 B1 | 8/2003 | Torres | |
| 6,648,909 B2 | 11/2003 | Helming | |
| D484,240 S | 12/2003 | Lyons et al. | |
| D484,985 S | 1/2004 | Takizawa et al. | |
| D486,603 S | 2/2004 | Larkin et al. | |
| 6,755,852 B2 | 6/2004 | Lachenbruch et al. | |
| D505,041 S | 5/2005 | Lesosky | |
| D507,056 S | 7/2005 | Friedland | |
| 6,916,334 B2 | 7/2005 | Noonan | |
| D512,511 S | 12/2005 | Friedland | |
| 6,972,029 B2 | 12/2005 | Mayrhofer et al. | |
| 7,022,130 B2 | 4/2006 | Gammons et al. | |
| D525,533 S | 7/2006 | Edwards | |
| D527,108 S | 8/2006 | Krahner | |
| D531,790 S | 11/2006 | Wurzburg | |
| D532,523 S | 11/2006 | Krahner et al. | |
| D533,668 S | 12/2006 | Brown | |
| D537,161 S | 2/2007 | Sinkiewicz | |
| 7,182,777 B2 | 2/2007 | Mills | |
| D538,974 S | 3/2007 | Eknoian et al. | |
| 7,195,660 B2 | 3/2007 | Little et al. | |
| 7,220,889 B2 | 5/2007 | Sigurjonsson et al. | |
| D545,441 S | 6/2007 | Miyachika et al. | |
| D548,405 S | 8/2007 | Purnell | |
| D550,852 S | 9/2007 | Hoffman et al. | |
| 7,291,164 B2 | 11/2007 | Peterman et al. | |
| D557,810 S | 12/2007 | Eknoian et al. | |
| D564,705 S | 3/2008 | Ohnishi et al. | |
| D565,740 S | 4/2008 | Sybrandts | |
| D569,035 S | 5/2008 | Eknoian et al. | |
| 7,370,689 B2 | 5/2008 | Wang | |
| D570,488 S | 6/2008 | Kirksey et al. | |
| D570,541 S | 6/2008 | Ohnishi et al. | |
| 7,393,336 B2 | 7/2008 | Sloot | |
| D574,962 S | 8/2008 | Atkins et al. | |
| D574,999 S | 8/2008 | Eknoian et al. | |
| D575,875 S | 8/2008 | Robinson et al. | |
| D576,282 S | 9/2008 | Yanaki | |
| D577,606 S | 9/2008 | Friedland et al. | |
| D588,703 S | 3/2009 | Boleratz | |
| D592,001 S | 5/2009 | Smith | |
| D596,305 S | 7/2009 | Usui et al. | |
| D597,678 S | 8/2009 | Wagner | |
| D605,299 S | 12/2009 | Iwahashi et al. | |
| D608,500 S | 1/2010 | Lu et al. | |
| 7,652,228 B2 | 1/2010 | Igaki et al. | |
| D613,181 S | 4/2010 | Friedland et al. | |
| D615,278 S | 5/2010 | Reed | |
| 7,707,655 B2 | 5/2010 | Braunecker et al. | |
| D616,760 S | 6/2010 | Deuerer | |
| D618,357 S | 6/2010 | Navies | |
| D618,811 S | 6/2010 | Navies | |
| D620,123 S | 7/2010 | Igwebuike | |
| D622,449 S | 8/2010 | Culley et al. | |
| D624,346 S | 9/2010 | Salzman | |
| D626,243 S | 10/2010 | Sagnip et al. | |
| D627,527 S | 11/2010 | Ferguson et al. | |
| D627,586 S | 11/2010 | Holdridge | |
| D629,589 S | 12/2010 | Mayo | |
| 7,854,712 B2 | 12/2010 | Evans et al. | |
| D630,376 S | 1/2011 | Yamamoto | |
| D634,473 S | 3/2011 | Koike | |
| D635,272 S | 3/2011 | Gruber et al. | |
| 7,937,909 B2 | 5/2011 | Carvallo | |
| D646,842 S | 10/2011 | Roman | |
| D647,146 S | 10/2011 | Islava | |
| D648,439 S | 11/2011 | Greener et al. | |
| D649,647 S | 11/2011 | Williams | |
| D651,719 S | 1/2012 | Kusmierz | |
| D656,235 S | 3/2012 | Howell | |
| D660,447 S | 5/2012 | Baltazar | |
| 8,226,699 B2 | 7/2012 | Evans | |
| D667,957 S | 9/2012 | Baumwald | |
| D668,343 S | 10/2012 | Baumwald et al. | |
| D668,344 S | 10/2012 | Baumwald et al. | |
| D668,345 S | 10/2012 | Baumwald | |
| 8,281,450 B2 | 10/2012 | Spain | |
| D670,816 S | 11/2012 | Suzuki et al. | |
| D671,225 S | 11/2012 | Higley | |
| D674,903 S | 1/2013 | Harder | |
| D676,469 S | 2/2013 | Vanettes, Jr. et al. | |
| D677,394 S | 3/2013 | Grust et al. | |
| D683,018 S | 5/2013 | Herivel et al. | |
| D693,015 S | 11/2013 | Dubbe | |
| 8,581,017 B2 | 11/2013 | Holm et al. | |
| D701,611 S | 3/2014 | Baumwald | |
| 8,887,962 B2 | 11/2014 | Herivel et al. | |
| D728,810 S | 5/2015 | Baumwald | |
| D738,576 S | 9/2015 | Harrell et al. | |
| D749,232 S | 2/2016 | Baumwald et al. | |
| D771,014 S | 11/2016 | Dubbe | |
| D787,080 S | 5/2017 | Baltazar | |
| D787,694 S | 5/2017 | Baltazar | |
| D793,569 S | 8/2017 | Baumwald | |
| D805,648 S | 12/2017 | Baumwald | |
| D818,596 S | 5/2018 | Zheng | |

(56) References Cited

U.S. PATENT DOCUMENTS

| | | | |
|---|---|---|---|
| D821,597 | S | 6/2018 | Martinez |
| D822,219 | S | 7/2018 | Coates et al. |
| D836,208 | S | 12/2018 | Dubbe |
| 2003/0064042 | A1 | 4/2003 | Bergquist et al. |
| 2004/0010302 | A1 | 1/2004 | Hoffmann et al. |
| 2004/0138601 | A1 | 7/2004 | Chalmers |
| 2004/0147991 | A1 | 7/2004 | Lu |
| 2005/0070980 | A1* | 3/2005 | Noonan .................. A61F 7/02 |
| | | | 607/108 |
| 2005/0187598 | A1 | 8/2005 | Shimizu et al. |
| 2006/0015052 | A1 | 1/2006 | Crisp |
| 2007/0021810 | A1 | 1/2007 | Paulin |
| 2007/0068508 | A1 | 3/2007 | Wong |
| 2007/0252115 | A1* | 11/2007 | Arehart .................. C09K 9/00 |
| | | | 252/583 |
| 2007/0262290 | A1 | 11/2007 | Beck et al. |
| 2008/0039763 | A1 | 2/2008 | Sigurjonsson et al. |
| 2008/0119916 | A1 | 5/2008 | Choucair et al. |
| 2008/0208299 | A1 | 8/2008 | Martineau |
| 2009/0048650 | A1 | 2/2009 | Junkins |
| 2009/0143516 | A1 | 6/2009 | MacDonald et al. |
| 2009/0163984 | A1 | 6/2009 | Robinson et al. |
| 2010/0010597 | A1 | 1/2010 | Evans |
| 2010/0010598 | A1 | 1/2010 | Igaki et al. |
| 2010/0217363 | A1 | 8/2010 | Whitely |
| 2012/0165910 | A1 | 6/2012 | Choucair et al. |
| 2013/0073018 | A1 | 3/2013 | Harwood et al. |
| 2014/0291585 | A1 | 10/2014 | Tozuka et al. |
| 2014/0316314 | A1 | 10/2014 | Schubert |
| 2014/0371829 | A1* | 12/2014 | Stine ...................... A61F 7/10 |
| | | | 607/108 |
| 2015/0173942 | A1 | 6/2015 | Whitely |

FOREIGN PATENT DOCUMENTS

| | | |
|---|---|---|
| CA | 146073 S | 4/2013 |
| CA | 146980 S | 7/2013 |
| CA | 156435 S | 2/2015 |
| CA | 160958 S | 12/2015 |
| CN | 103242820 A | 8/2013 |
| CN | 103788939 A | 5/2014 |
| CN | 105400359 A | 3/2016 |
| CN | 105713597 A | 6/2016 |
| CN | 106750466 A | 5/2017 |
| CN | 107325220 A | 11/2017 |
| CN | 107550627 A | 1/2018 |
| CN | 107647962 A | 2/2018 |
| CN | 108440883 A | 8/2018 |
| DE | 202008004774 U1 | 7/2008 |
| EP | 162583 B1 | 11/1985 |
| JP | 2006045408 A * | 2/2006 |
| JP | 2006045408 A | 2/2006 |
| JP | 2006045464 A * | 2/2006 |
| JP | 2006045464 A | 2/2006 |
| KR | 20170024708 A | 3/2017 |
| WO | 2001078797 A1 | 10/2001 |
| WO | 2016093788 A1 | 6/2016 |

OTHER PUBLICATIONS

Entire prosecution history of U.S. Appl. No. 12/794,576.
Entire prosecution history of U.S. Appl. No. 29/402,951.
Entire prosecution history of U.S. Appl. No. 29/402,971.
Entire prosecution history of U.S. Appl. No. 29/402,974.
Entire prosecution history of U.S. Appl. No. 29/403,056.
Entire prosecution history of U.S. Appl. No. 29/403,478.
Entire prosecution history of U.S. Appl. No. 29/406,622.
Entire prosecution history of U.S. Appl. No. 29/406,623.
Entire prosecution history of U.S. Appl. No. 29/406,624.
Entire prosecution history of U.S. Appl. No. 29/410,928.
Entire prosecution history of U.S. Appl. No. 29/410,930.
Entire prosecution history of U.S. Appl. No. 29/413,705.
Entire prosecution history of U.S. Appl. No. 29/429,143.
Entire prosecution history of U.S. Appl. No. 29/429,147.
Entire prosecution history of U.S. Appl. No. 29/429,154.
Entire prosecution history of U.S. Appl. No. 29/429,157.
Entire prosecution history of U.S. Appl. No. 29/431,148.
Entire prosecution history of U.S. Appl. No. 29/431,399.
Entire prosecution history of U.S. Appl. No. 29/433,566.
Entire prosecution history of U.S. Appl. No. 29/433,567.
Entire prosecution history of U.S. Appl. No. 29/433,568.
Entire prosecution history of U.S. Appl. No. 29/433,570.
Entire prosecution history of U.S. Appl. No. 29/433,806.
Entire prosecution history of U.S. Appl. No. 29/433,907.
Entire prosecution history of U.S. Appl. No. 29/433,805.
Entire prosecution history of U.S. Appl. No. 29/434,757.
Entire prosecution history of U.S. Appl. No. 29/434,760.
Entire prosecution history of U.S. Appl. No. 29/434,763.
Entire prosecution history of U.S. Appl. No. 29/435,893.
Entire prosecution history of U.S. Appl. No. 29/435,896.
Entire prosecution history of U.S. Appl. No. 29/435,900.
Entire prosecution history of U.S. Appl. No. 29/435,901.
Entire prosecution history of U.S. Appl. No. 29/480,356.
Entire prosecution history of U.S. Appl. No. 29/498,780.
Entire prosecution history of U.S. Appl. No. 29/498,781.
Entire prosecution history of U.S. Appl. No. 29/498,785.
Entire prosecution history of U.S. Appl. No. 29/498,786.
Entire prosecution history of U.S. Appl. No. 29/499,977.
Entire prosecution history of U.S. Appl. No. 29/558,747.
Entire prosecution history of U.S. Appl. No. 29/558,750.
Entire prosecution history of U.S. Appl. No. 29/558,755.
Entire prosecution history of U.S. Appl. No. 29/558,760.
Entire prosecution history of U.S. Appl. No. 29/644,299.
Entire prosecution history of U.S. Appl. No. 29/644,302.
Entire prosecution history of U.S. Appl. No. 29/644,303.
Entire prosecution history of U.S. Appl. No. 29/647,787.
https://www.itamed .com/our-products/maternity-women-s-health-collection/post-surgical.html, printed Sep. 13, 2004.
Int'l Search Report & Written Opinion, PCT/CN2018/077916 (ISA-CN dated Dec. 3, 2018).
Kendall Obstetric & Neonatal Products Brochure, Jan. 2004 ed.
CA 3002264, Office Action (Canadian Intellectual Property Office dated Jul. 29, 2019).
Supp. European Search Report and Opinion, App. EP 18907888.4 (E.P.O. dated Apr. 2, 2020).
Office Action (and reference cited) issued in U.S. Appl. No. 29/435,900 dated Sep. 25, 2020.
Office Action (and reference cited) issued in U.S. Appl. No. 29/435,901 dated Sep. 25, 2020.
Office Action (and references cited) issued in U.S. Appl. No. 15/844,977 dated Jun. 12, 2020.
AU 2018232917, Examination Report (Australian Intellectual Property Office dated Aug. 14, 2020).
Palcare Catalog: 2008 Presentations (attached).
PCT/US2017/38880, Written Opinion of the International Search Authority (opinion dated Nov. 17, 2017).
Document entitled: "Theramal Gel Beads Innovations: the easier way to enjoy a cozy & effective relief"; author unknown; authenticity unknown and in question; unknown if ever published; date of creation unknown and in question. Disclosed by Applicant in abundance of caution.

* cited by examiner

POLYMERS, THERMOCHROMIC AGENTS, AND/OR HYDROGEL COMPOSITIONS AND APPARATUS, INCLUDING PRODUCTS EMBODYING THE SAME, AND METHODS AND PROCESSES FOR MAKING SAME

RELATED APPLICATION DATA

This application is a divisional of U.S. patent application Ser. No. 15/986,790, filed on May 22, 2018, which is a continuation of International Application No. PCT/CN2018/077916, filed on Mar. 2, 2018 with the China Intellectual Property Office as the Receiving Office, which designated all contracting states bound by the Patent Cooperation Treaty on the international filing date. All claims of priority available are hereby made, and the entirety of each application identified above is hereby incorporated by reference.

TECHNICAL FIELD

The inventions described herein relate to polymers, hydrogels, and thermochromic agents, including products embodying them, methods of using them, and processes for making them. In certain embodiments, the inventions disclosed relate to temperature therapy packs which utilize thermochromic agents integrated into solid, semi-solid, or liquid hydrogels. In preferred (but optional) embodiments, the inventions described herein relate to thermochromic agents integrated into one or more compositions used as the temperature exchange material of a therapy pack. In certain other embodiments, the inventions described herein relate to methods of using the thermochromic integrated temperature exchange materials, or processes for manufacturing such thermochromic integrated temperature exchange materials and/or methods or processes for manufacturing or using thermal packs embodying such materials. In certain particularly preferred embodiments, one or more inventions described herein relate to novel polymer compositions and/or processes for making polymers, where product durability or longevity is improved and/or in which number of use cycles is improved or where usage times are increased.

BACKGROUND OF THE DISCLOSURE

The term of art "thermochromic", as used throughout this specification, generally refers to pigments or dyes which, when exposed to changes in temperature, experience a change in color. Similarly, the term "reversible" when used to describe such pigments or dyes, reflects that the color changes obtained during thermal cycling may be reversed. Thermochromic pigments or dyes (or generally "thermochromic agents") are known in a variety of arts ranging from the field of novelty items to the medical industry. Generally, thermochromic agents are used to either add or create aesthetic effects with no practical purpose other than entertainment, or are used as an indicator, of sorts, to identify temperature changes in items in which the thermochromic agents are embodied or otherwise utilized.

For example, U.S. Pat. No. 5,219,625 ("Matsunami") discloses the use of thermochromic materials for application to clothing and toys for entertainment purposes. On the opposite end of the spectrum, International Publication No. WO 2016/093788 ("Isildak") teaches the use of thermochromic agents to image blood vessels, such as to identify cancerous tumors which (according to the publication) include higher densities of blood vessels, for example. U.S. Publication No. 2009/0143516 ("MacDonald") also teaches the use of thermochromic agents in the medical field, but in the implementation of such agents into gloves, so as to be able to determine whether a surgical glove is punctured. In still other uses of thermochromic agents, U.S. Publication No. 2014/0291585 ("Tozuka") teaches to introduce thermochromic agents into the ink of writing instruments, so that if a mistake is made while writing, the writing ink (which includes thermochromic pigment) can be heated through friction to make the ink visually disappear.

In addition to the above uses, there is limited knowledge in the art of the use of thermochromic agents in the field of temperature therapy. For example, U.S. Publication No. 2013/0073018 ("Harwood") teaches the use of thermochromic films applied to a thermal pack "cover" or "covering" for notifying the user as to when the pack is ready for use. However, the Harwood reference has many disadvantages which the applicants herein have addressed or solved with the present application for invention. For example, a thermal pack covering is not an accurate representation of the temperature of the therapy pack, nor is it a reliable indicator that the therapy pack is ready for therapeutic use. A thermal pack covering is exposed to ambient air and is also exposed to the skin of a pack user, or to a refrigerator surface, or table, or other surface, which the covering contacts when the thermal pack is chilled for use or placed on a surface prior to use. Therefore, the thermal pack coverings taught in Harwood are likely to change color at times responsive to (or at least impacted by) ambient air or skin (or other surface) temperatures, in contrast to providing an accurate measure of the temperature of the "core" of the temperature therapy pack itself. Consequently, the user of a pack, such as disclosed in Harwood, is likely to be misled by the color changing features disclosed therein. This is particularly true of the embodiments disclosed in Harwood in which a thermochromic agent is introduced into a fabric cover which is enshrouded over the disclosed temperature therapy packs to impart a particular aesthetic appearance (see, i.e., Harwood, para. [0029]).

The "temperature exchange material" of a thermal pack is the payload of the thermal pack which stores the hot or cold temperature (heat, or lack thereof in the case of a cold pack) for transfer to the skin or body part of an end user. Notably, Harwood nowhere teaches to integrate thermochromic agents into the temperature exchange material of a thermal pack itself. Moreover, Harwood nowhere teaches how to technically implement such an integration into the thermal exchange material of a thermal pack, or how to manufacture such a thermal pack. In particular, the applicants of the present invention have discovered that there are numerous difficulties and obstacles in doing so.

The applicants of the present invention have also discovered problems in the prior art pertaining to hydrogels, including the durability of hydrogels in semi-solid or solid form. Moreover, the applicants of the inventions disclosed herein have discovered that there are needs in the art for hydrogels, in solid, semi-solid, and/or fluid gel form, which durably integrate thermochromic agents. More generally, applicants have also discovered a need for polymers which integrate thermochromic agents which have improved lifespans (e.g., in storage and otherwise) and/or which have increased numbers of available use cycles and/or which exhibit improved usage times.

In view of the above-identified deficiencies in the art, the applicants for the inventions described herein have addressed, overcome, or solved such deficiencies (in whole or in part) with one or more of the below described methods, processes, or apparatus. It is, in certain embodiments, a purpose of the herein described methods, processes, or apparatus to address one or more of the above deficiencies or needs in the art. It is also a purpose of the herein described methods, processes, or apparatus to address other drawbacks and/or other desires for improvements in the art, whether or not currently known, which will become more apparent to the skilled artisan once given the present disclosure.

SUMMARY OF INVENTION

This invention, in some embodiments, relates to improvements in polymers, and/or to the use of thermochromic agents (e.g., such as thermochromic pigments or dyes) combined with or in conjunction with polymers. In other embodiments, this invention relates to therapy packs which deliver hot/cold temperature therapy to body parts of users. In preferred embodiments, hot/cold temperature therapy packs are provided which include or employ thermochromic agents. In certain other embodiments, the described inventions relate to hydrogels, including hydrogels in semi-solid, solid, and fluid form, which exhibit improved durability and/or which integrate or otherwise contain thermochromic agents. In certain preferred embodiments, these improved hydrogels, combined with thermochromic agents, are used as one or more temperature exchange materials of hot/cold temperature therapy packs.

In preferred embodiments, this application relates to novel thermochromic polymer or hydrogel compositions as well as processes for manufacturing such polymers or hydrogels to have useful thermochromic properties. In these embodiments, processes and methods for usefully and (preferably) durably integrating thermochromic agents into polymers and hydrogels are provided. In related embodiments, this application pertains to apparatus, such as temperature therapy packs, which are manufactured using the herein disclosed thermochromic compositions and/or using the herein described novel manufacturing methods and processes. Regardless of whether apparatus, method, or process, the applicants consider each and all of these embodiments (independently or combined) to be one or more aspects of their invention.

Although the applicants for this invention envision certain embodiments to be most preferred, any use of the term "preferred" is not intended to be limiting in any fashion. Moreover, the word "embodiment" should be broadly construed as reflecting an example of a genus or species of the inventions described herein. That is, regardless of whether described as "preferred" or as an "embodiment" (or as a "preferred embodiment"), the examples to which these terms refer are nevertheless optional, and variants therefrom are still considered by the applicants to be within the scope of their invention.

In one such example (i.e., optional) preferred embodiment, a temperature therapy pack is provided which utilizes hydrogel, formed into a plurality of beads (or microspheres) as a fill material to provide temperature exchange properties. In this embodiment, the hydrogel beads are installed into a preferably transparent therapy pack shell, such that the hydrogel beads are visually viewable by a user of the therapy pack. Moreover, in this preferred example, the hydrogel beads include or otherwise utilize one or more thermochromic agents (e.g., integrated into the beads), so that the beads will display useful color changing effects upon exposure to changes in temperature.

As an example utility for this preferred embodiment, temperature therapy packs filled (partially or fully) with hydrogel (in bead or fluid gel form) are constructed, utilizing a particularly selected thermochromic composition (or combination of thermochromic agents), so that the thermochromic agents provide one or more visual indicia to a user. Specifically, the thermochromic agents, or combinations thereof, are preferably selected to indicate that the therapy pack is sufficiently hot or cold for providing hot or cold temperature therapy to a user, respectively. Conversely, if the therapy pack is not hot or cold enough for temperature therapy, the pack is preferably designed to indicate this lack of readiness with a separate color, imparted by the thermochromic agents, or simply a lack of color (due to decolorization of the thermochromic agent). For example, in applicants' most preferred embodiment, a temperature therapy pack is constructed of a transparent pack shell so that the thermochromic hydrogel beads contained in the pack gel are visible to a user. In this most preferred embodiment, the hydrogel beads appear blue when the therapy pack is not ready to provide temperature therapy (e.g., when they are at or near conventional room temperature). In contrast, when the hydrogel beads of the therapy pack appear as white or clear, the beads (acting as the thermal exchange material) have been sufficiently heated to provide heat therapy to a user. In certain preferred embodiments, the packs can be microwaved to heat them prior to use. However other methods of heating the packs may also be used, such as by placing the packs in hot water. Similarly, when the hydrogel beads of the therapy pack display the color purple, the beads have been sufficiently cooled (e.g., in a freezer, or in a cold water bath) to provide cold therapy to a user. Of course, other color combinations or schemes can be selected and used for providing temperature (or other status) indicia by selecting different thermochromic pigments or by otherwise tailoring the combination or composition of thermochromic agents used.

When the applicants for the herein disclosed inventions embarked on the process of creating the novel temperature therapy packs described herein, many unexpected obstacles and problems were encountered during the development process. For example, the thermochromic properties of the hydrogel beads which were impregnated with thermochromic agents had insufficient longevity (e.g. experienced color fading), and/or the hydrogel beads themselves exhibited poor structural durability. Such problems were exacerbated when the hydrogel beads were installed in prototype therapy packs which included lubricant (e.g., water) and/or antifreeze compositions so that the hydrogel beads would be permitted to move freely amongst other beads, and/or so that the lubricant would not freeze solid which cooled in a freezer. Other problems encountered pertained to the disbursement of thermochromic pigments within the hydrogels both evenly and in sufficient quantity to obtain product uniformity and/or sufficient thermochromic visual effect for adequately assisting with thermal therapy, respectively.

In order to solve these unforeseen problems, the applicants for the herein described inventions unpredictably discovered that reversible thermochromic properties could be obtained with sufficient longevity, and that improved hydrogel bead durability could be obtained, using novel manufacturing processes and/or compositions described herein. These novel compositions and processes include, but are not limited to, the novel hydrogel compositions disclosed herein, as well as methods and processes for manufacturing or processing the hydrogel beads. These compositions and/or processes allow a reversibly thermochromic temperature therapy pack to be manufactured which has a suitably long "shelf life" so that it can be successfully commercialized, without loss of significant product performance due to the passage of time when the product is shipped or is sitting on stores shelves prior to use. These uniquely made, novel temperature therapy packs are (optionally) also capable of of changing color, through thermal cycling, in a greater number of use cycles. Moreover, the duration of color display is also improved.

Embodying the above or other improvements in the art, at least one embodiment of the herein disclosed inventions provides: a temperature therapy pack for providing hot and cold temperature therapy to a body part, and which displays color to indicate different therapy pack temperatures, comprising: a visually transparent temperature therapy pack enclosure; a first thermochromic agent having properties selected to display a first color X within a baseline temperature range T1 inclusive of room temperature, which de-colors above a temperature T2; a second thermochromic agent having properties selected to display a second color Y below a temperature T3 which is below the baseline temperature range T1, which de-colors above the temperature T3; a pack fill material being combined with the first and the second thermochromic agents to collectively comprise a reversible thermochromic, thermal exchange material, the reversible thermochromic, thermal exchange material being enclosed in the visually transparent temperature therapy pack enclosure; the temperature therapy pack being so configured such that when it is heated or cooled, the thermal exchange material retains heat or cold, respectively, so that the temperature therapy pack can be applied to a body part of a user to provide hot or cold temperature therapy; and wherein when the thermal exchange material of said temperature therapy pack is measurable at a temperature within the temperature range T1, the temperature therapy pack displays the first color X; when the thermal exchange material of the temperature therapy pack is measurable at a temperature above the temperature T2, the first and the second thermochromic agents each de-color; and when the thermal exchange material of the temperature therapy pack is measurable at a temperature below the temperature T3, the first color X and the second color Y, of the first and second thermochromic agents, respectively, each simultaneously display and thereby spectrally combine such that the temperature therapy pack displays a third color Z, which is a result of the spectral combination of colors X and Y.

In an alternative embodiment, there is provided: a temperature therapy pack for providing hot and cold temperature therapy to a body part, and which displays color to indicate different therapy pack temperatures, comprising: a visually transparent temperature therapy pack enclosure; a first thermochromic agent having properties selected to display a first color X within a first temperature range, which de-colors outside of the first temperature range; a second thermochromic agent having properties selected to display a second color Y within a second temperature range, which de-colors outside of the second temperature range;
a pack fill material being combined with the first and the second thermochromic agents to collectively comprise a reversible thermochromic, thermal exchange material, the reversible thermochromic, thermal exchange material being enclosed in the visually transparent temperature therapy pack enclosure; the temperature therapy pack being so configured such that when it is heated or cooled, the thermal exchange material retains heat or cold, respectively, so that the temperature therapy pack can be applied to a body part of a user to provide hot or cold temperature therapy; and the first and the second thermochromic agents being particularly configured and selected such that when the thermal exchange material of the temperature therapy pack is measurable at a temperature within a temperature range T1, the temperature therapy pack displays a first color A; when the thermal exchange material of the temperature therapy pack is measurable at a temperature above the temperature range T1, the temperature therapy pack displays a second color B; and when the thermal exchange material of the temperature therapy pack is measurable at a temperature below the temperature range T1, the temperature therapy pack displays a third color C; and
wherein one of the first, second, or third colors A, B, or C respectively is a color obtained through the spectral combination of the other two colors, such that three temperature therapy pack display colors are obtained utilizing only two thermochromic agents.

In a particular preferred, yet still optional embodiment embodying the herein described improvements in the art, the reversible thermochromic materials developed by the applicants comprise the following compositions by mass fraction: polymer in the amount of 5%-40%; thermochromic powder in the amount of 1%-7%; dispersing agent in the amount of 1.5%-33%; dispersing auxiliary in the amount of 1.5%-35%; solvent in the amount of 5%-30%. Preferably, in this example, the polymer comprises at least one of the following components: polyacrylic acid polymer, natural polymer, and cellulose derivatives.

In at least one embodiment, the above-disclosed reversible thermochromic material (or composition) is used as part of a temperature therapy pack. In one such embodiment, for example, there is provided: a temperature therapy pack comprising: a temperature exchange material enclosed in a temperature therapy pack enclosure for providing temperature therapy to a user, the temperature exchange material being combined with a thermochromic agent, the combination of the temperature exchange material and the thermochromic agent comprising a reversible thermochromic, therapeutic material comprising, by mass fraction: polymer in the amount of 5%-40%; thermochromic powder in the amount of 1%-7%; dispersing agent in the amount of 1.5%-33%; dispersing auxiliary in the amount of 1.5%-35%; solvent in the amount of 5%-30%; and wherein the polymer comprises at least one of the following components: polyacrylic acid polymer, natural polymer, and cellulose derivatives.

In certain example embodiments which utilize the reversible thermochromic material described above, the polyacrylic acid polymer may optionally comprise at least one of the following components: polyacrylic acid, sodium polyacrylate, polyacrylamide, acrylamide/sodium acrylate copolymer, acrylamide/ethyl ammonium chloride acrylate copolymer, acrylamide/ethyl trimethyl ammonium chloride acrylate/ethyl ammonium chloride acrylate copolymer, acrylamide/sodium acrylate copolymer, acrylamide/sodium acryloyl dimethyl taurate copolymer, acrylic ester/acetoacetoxyethyl methacrylate copolymer, acrylic ester/beheneth-25 methacrylate copolymer, acrylic ester/beheneth-25 methacrylate/HEMA cross-linked polymer, acrylic ester/beheneth-25 methacrylate/HEMA cross-linked polymer-2, acrylic ester/C5-8 alkylacrylate copolymer, acrylic ester/C10-30 alkylacrylate cross-linked polymer, acrylic ester/C10-3 alkyl methacrylate copolymer, acrylic ester/ceteareth-20 methacrylate cross-linked polymer, acrylic ester/ceteareth-20 itaconate copolymer, acrylic ester/ceteareth-20 methacrylate polymer, acrylate cross-linked polymer-3, acrylate cross-linked polymer 4, acrylic ester/lauryl alcohol polyether-25 methacrylate copolymer, acrylic ester/lauryl alcohol polyether-25 acrylate copolymer, acrylic ester/lauryl alcohol polyether-25 itaconate, acrylic ester/stearyl alcohol polyether-50 acrylate copolymer, acrylic ester/stearyl alcohol polyether-20 itaconate copolymer, acrylic ester/stearyl alcohol polyether-20 methacrylate copolymer, acrylic ester/stearyl alcohol polyether-30 methacrylate copolymer, acrylic ester/stearyl methacrylate copolymer, acrylic ester/vinyl isodecanoate cross-linked polymer, acrylic ester/vinyl neodecanoate cross-linked polymer, acrylic acid/acrylonitrile copolymer, acrylic acid/phosphorylcholine glycol acrylate cross-linked polymer, ammonium acrylic ester/acrylonitrile copolymer, ammonium acrylate copolymer, ammonium acryloyldimethyltaurate/carboxylic ethyl acrylate cross-linked polymer, ammonium acryloyldimethyltaurate/stearyl alcohol polyether-8 methacrylate copolymer, C18-22 alkyl PEG-25 methacrylate/2-Diethylaminoethyl methacrylate copolymer, glyceryl acrylate/acrylic acid copolymer, HEA/sodium acryloyldimethyltaurate/stearyl alcohol polyether-20 methacrylate copolymer, potassium polyacrylate, sodium acrylate/acrylaldehyde copolymer, sodium acrylate/acrylonitrile copolymer, sodium acrylate/acryloyldimethyltaurate/dimethylacrylamide cross-linked polymer, sodium acrylate/beheneth-25 methacrylate cross-linked polymer, sodium acrylate copolymer, sodium acrylate/sodium acrylamide methylpropane sulfonate copolymer, sodium acrylate/sodium acryloyldimethyltaurate/acrylamide copolymer, sodium acrylate/sodium acryloyldimethyltaurate copolymer, sodium acrylate/vinyl isodecanoate cross-linked polymer, sodium acrylate/vinylacetamide copolymer, sodium acrylate/vinyl alcohol copolymer, sodium acryloyldimethyltaurate/acrylamide/VP copolymer, sodium styrol/acrylate copolymer, sodium polymethacrylate, sodium polyacrylate starch, sodium taurate acrylate/acrylic acid/acrylonitrile copolymer, starch/acrylate/acrylamide copolymer, and tromethamine acrylate/acrylonitrile copolymer.

Although not in all embodiments, in certain preferred embodiments, the polyacrylic acid polymer described above is (preferably) generated from the reaction of monomers with initiators. In at least one of such embodiments, the monomers include acrylic acid and the relevant acrylate, acrylamide and acrylic ester, and the initiators include potassium persulfate, ammonium persulfate, tert butyl hydroperoxide and dimethyl sulfonyl peroxide. In particularly preferred (but still optional) embodiments, the mass ratio of the monomer and initiator ranges from 50:1-200:1. As a further beneficial but optional preference, the raw materials for the polymerization of polyacrylic polymer also include a crosslinking agent, which includes N,N'-methylene bisacrylamide. Moreover, the preferred mass ratio of the crosslinking agent to monomer is approximately 1:100-1:200.

In preferred, but still optional embodiments of the reversible thermochromic aspects of the inventions described herein, it has been found useful to use natural polymers comprising at least one of the following components: agar, ammonium alginate, algin, alginic acid, amylopectin, gum tragacanth, calcium alginate, carrageenen, cassia gum, locust bean gum, quinoa starch, Guar bean gum, dehydroxanthan gum, alsace gum, carrageenin, gelatine, Gellan gum, Ghatti gum, magnesium alginate, Natto gum, pectine, potassium alginate, potassium carrageenan, peach gum, Rhizobian gum, Sclerotium gum, sodium carraghenate, gum sterculia, Tamarindus Indica seed gum, tapioca, TEA-alginate, Welan gum, and Xathan gum. In the most preferable embodiments, the natural polymer is at least one polymer selected from the group comprising: agar, ammonium alginate, carrageenan, gelatin, Gellan gum and Xathan gum. Such natural polymers have a long-chain macromolecule structure and excellent thickening and gelling effects. Used in the novel processes and compositions described herein, they wrap the thermochromic powder effectively, with no destructive effect on the thermochromic powder, thereby obtaining stronger structure and longer thermochromic life.

In combination with the optional embodiments described above, or in other embodiments described elsewhere herein, the cellulose derivatives utilized in the reversible thermochromic materials may optionally comprise: oxyhydroxypropyl cetyl hydroxyethylcellulose, calcium carboxymethylcellulose, C12-16 alkyl PEG-2 hydroxypropyl hydroxyethyl ethylcellulose, carboxymethyl cellulose acetate butyrate, carboxymethyl hydroxyethyl cellulose, cellulolytic enzyme, cellulose acetate propionate, calcium octenyl succinate starch, glyceryl alginate, hydrolyzed cellulose gum, hydroxyethyl chitosan, hydroxypropyl chitosan, hydroxypropyl guar gum, hydroxypropyl starch, hydroxypropyl starch phosphate, hydroxypropyl xanthan gum, ethyloic chitin, carboxymehyl chitosan, sodium carboxymethyl chitin, sodium carboxymethyl dextrin, sodium polygluconate, carboxymethyl starch sodium, carboxymethyl glucosan, sodium starch octenyl succinate, starch hydroxypropyl trimethyl ammonium chloride, hexadecyl hydroxyethyl cellulose, croscarmellose, carboxymethyl hydroxypropyl guar gum, ethyl cellulose, sodium carboxymethyl cellulose, hydrogenated bovine base benzyl dimethyl bentonite, hydroxybutyl methyl cellulose, hydroxyethyl cellulose, hydroxy propyl cellulose, hydroxypropyl methylcellulose, methyl cellulose, methyl ethyl cellulose, methyl hydroxyethyl cellulose, microcrystalline cellulose, nonylphenol polyether hydroxyethyl cellulose, oxycellulose, sodium cellulose sulfate, and/or stearoxy PG-hydroxyethylcellulose sulfonate. Most preferably, the cellulose derivative is one or more of the materials selected from the group comprising: calcium carboxymethyl cellulose, carboxymethyl hydroxyethyl cellulose, sodium carboxymethyl cellulose, hydroxyethyl cellulose, hydroxypropyl cellulose and hydroxypropyl methylcellulose. Used in the compositions and processes described herein, such cellulose derivatives have excellent thickening effect. Like the natural polymers specified supra for applicant's compositions and processes, they also wrap the thermochromic powder effectively, with no destructive effect on the thermochromic powder. This results in a stronger structure and longer thermochromic life.

In certain embodiments, the reversible thermochromic materials described herein (preferably) use a dispersing agent comprising Tween-20, -40, -60, -80 and -85 and Span-40, -60 and -80. In such or other preferred embodiments, the dispersing auxiliary may optionally comprise allyl alcohol, n-propanol, butanetriol, polyethylene glycol and/or polyglycerol. In the most preferred embodiments, the dispersing auxiliary is allyl alcohol, n-propanol or butanetriol. Use of these most preferred dispersing auxiliaries unexpectedly obtains better dispersing performance, resulting in more uniform color and longer life.

In some embodiments of the invention, it has been found useful to utilize thermochromic agents in the form of thermochromic powder. In example embodiments using such thermochromic powder, the identity of the powder may be selected so that the material either develops or changes color when heated or cooled (thermal color-developing type) or loses color when heated or cooled (thermal de-coloring type). In still other embodiments, blends of powders or other thermochromic agents may be used to obtain a plurality of thermochromic or color changing effects, all in the same product. Preferably, the chromogenic temperature section of the thermochromic powder is in any temperature range of −20° C. to 80° C. The thermochromic powder is distinguished by using the temperature color change thresholds to characterize the powder.

The method for preparing the reversible thermochromic material disclosed herein includes the following process steps: uniformly mixing the polymers, dispersing agent, dispersing auxiliary, thermochromic powder, and solvent. In a particularly efficacious example, applicant determined that the premixing the thermochromic powder, in the following process, produces particularly desirable compositions and functional results: premix the thermochromic powder with dispersant, solvent and dispersing auxiliary to obtain a thermochromic color paste. Then, mix the thermochromic color paste with polymer to obtain a gel composition. Using this preparation step, described in more detail in the DETAILED DESCRIPTION section of the specification, uniform dispersion of the thermochromic agent within the gel composition is more readily obtained.

In an alternative embodiment, the thermochromic gel composition may be prepared as follows: mixing the dispersing agent, dispersing auxiliary, solvent and thermochromic powder. The resulting mixture is then added to the solution containing monomers and initiators and used for preparing said polymers to gain mixed liquid. The liquid is then added drop by drop into the oil to allow the polyreaction. Afterwards, upon completion of the polyreaction, the products generated are cleaned and dried to form the thermochromic material.

In certain preferred embodiments, the solvent utilized to manufacture the reversible thermochromic material may comprise at least one of the following components: water, glycerin, ethanol and propylene glycol.

When developing the herein described products and processes, the applicants for the herein disclosed inventions discovered that pigment particle size was a significant factor in obtaining suitable product performance and durability. More specifically, applicants have unexpectedly discovered that if the particle size is too large, particles do not effectively disperse in the polymers and gels described herein, which can lead to gel structural failure (e.g., particularly where the polymers are formed into semi-solid forms, such as beads). Further, if the particle size is too small, the displayed color is faint and/or the thermochromic life is short due to the small amount of coated thermochromic material. Moreover, using thermochromic powder of small particle size entails more stringent process preparation parameters, and lower yield is obtained. In addition, it has been discovered that the use of too small particle sizes is an obstacle to obtaining sufficiently long storage life in the final product. Consequently, applicants have discovered a heretofore unknown useful range of beneficial thermochromic pigment particle sizes, generally between 5-20 micrometers, which unexpectedly provide the advantages described elsewhere herein. Thus, thermochromic powders with a grain (or particle) size between 5-20 micrometers are most preferably used. But, grain size may also be between approximately 3-25 micrometers or between approximately 1-30 micrometers.

Thermochromic colorants may be made of from a wide range of molecules including, for example, spiropyrans, spirooxazines, lactones, spirolactones, diazarhodamine lactones, fulgides, chromenes, azobenzenes, quinones, styrylquinolines, fluorans, bianthrones, polythiophenes, polysilanes, polydiacetylenes, phenolphthaleins, merocyanines, anils, diphenylmethane phthalides, phenylindolylphthalides, indolylphthalides, diphenylmethane azaphthalides, phenylindoly-lazaphthalides, dihydroazulenes, vinylheptafulvenes, quinazolines, bisquinazolines, tri substituted pyridines, liquid crystals, and combinations thereof. More specific examples may include 6-nitro-1',3',3'-trimethylspiro-[2H-1-benzopuran-2,2'-indoline]; (E)-2-[1-(2,5-dimethyl-3-furyl)]ethylidene-(Z)-3-ethylidene-succinic anhydride; 1,2-dicyano-1,2-bis-(2,4,5-trimethyl-3-thienyl) ethane; 2,3-bis(2,4,5-trimethyl-3-thienyl)maleic anhydride; 3,3-bis(pdimethylaminophenyl)-6-dimethylaminophthalide; 3-(4-diethylaminophenyl)-3-(1-ethyl-2-methylindol-3-yl) phthalide; 3,3-bis(1-n-buty-1-2-methylindol-3-yl)phthalide; 3,3-bis(2-ethoxy-4-diethylaminophenyl)-4-azaphthalide; 3-[2-ethoxy-4-(N-ethylanilino)phenyl]-3-(1-ethyl-2-methylindol-3-yl)-4-azaphthalide; 3,6-dimethoxyfluoran; 3,6-di-n-butoxyfluoran; 2-methy-1-6-(N-ethyl-N-ptolylamino) fluoran; 3-chloro-6-cyclohexylaminofluoran; 2-methyl-6-cyclohexylaminofluoran; 2-(2-chloroanilino)-6-di-n-butylaminofluoran; 2-(3-trifluoromethylanilino)-6-diethylaminofluoran; 2-(N-methylanilino)-6-(N-ethyl-Np-tolylamino) fluoran, 1,3-dimethyl-6-diethylaminofluoran; 2-chloro-3-methyl-6-diethylaminofluoran; 2-anilino-3-methyl-6-diethylaminofluoran; 2-anilino-3-methyl-6-di-n-butylaminofluoran; 2-xylidino-3-methyl-6-diethylaminofluoran; 1,2-benzo-6-diethylaminofluoran; 1,2-benzo-6-(N-ethyl-N-isobutylamino)fluoran; 1,2-benzo-6-(N-ethyl-N-isoamylamino)fluoran; 2-(3-methoxy-4-dodecoxystyryl)quinoline; spiro[5H-(1)benzopyrano(2,3-d)pyrimidine-5,1'(3'H) isobenzofuran]-3'-one; 2-(diethylamino)-8-(diethylamino)-4-methylspiro[5H-(1)benzopyrano(2,3-d)pyrimidine-5,1' (3'H)isobenzofuran]-3'-one; 2-(di-nbutylamino)-8-(di-n-butylamino)-4-methyl-spiro[5H-(1)benzopyrano(2,3-d) pyrimidine-5,1'(3'H)isobenzofuran]-3'-one; 2-(di-n-butylamino)-8-(diethylamino)-4-methyl-spiro[5H-(1) benzopyrano(2,3-d)pyrimidine-5,1'(3'H)isobenzofuran]-3'-one; 2-(di-n-butylamino)-8(N-ethyl-N-isoamylamino)-4-methyl-spiro[5H-(1)benzopyrano(2,3-d)pyrimidine-5,1' (3'H)isobenzofuran]-3'-one; 2-(di-nbutylamino)-8-(di-n-butylamino)-4-phenyl, and combinations thereof.

In addition to organic molecules, inorganic compounds can also produce thermochromic responses such as: $Ag_2Hg_2I_4$, $Cu_2HgI_4$, and $SrCO_3$ and $MnO_2$ composite resins. In certain cases, the use of solutions of inorganic compounds such as $CoCl_2$ can be used to synthesize thermochromic materials in the presence of unsaturated esters, peroxides, and an accelerator.

In accordance with the above teachings, at least one optional method for obtaining the advantages described herein (or other advantages not yet contemplated) is provided as a method of manufacturing a thermal pack comprising: i) providing the following materials in amounts, determined by mass fraction, comprising: polymer in an amount of approximately 5%-40%; thermochromic powder in an amount of approximately 1%-7%; dispersing agent in an amount of approximately 1.5%-33%; dispersing auxiliary in an amount of approximately 1.5%-35%; solvent in an amount of approximately 5%-30%; and ii) preparing a thermal exchange material by performing the following steps: mixing the dispersing agent, the dispersing auxiliary, the solvent, and the thermochromic powder, to obtain a thermochromic composition; mixing the thermochromic composition with a polymer pre-cursor material, to obtain a mixed liquid; maintaining a pH of the mixed liquid between approximately 3-10; initiating polymerization of the mixed liquid at a temperature selected between approximately 40-88° C., to obtain a reversible thermochromic polymeric thermal exchange gel material; iii) installing the reversible thermochromic polymeric thermal exchange gel material into a visually transparent temperature therapy pack enclosure.

As an additional optional feature of the embodiments described herein, applicants discovered that ultraviolet light negatively impacted product durability and performance. Therefore, in some preferred (but still optional) embodiments, ultraviolet coatings or filtering layers are utilized, such as applied on the transparent thermal pack shell (or elsewhere).

Certain examples of the invention are now described below, with respect to certain non-limiting embodiments thereof, as illustrated in the following drawings wherein:

BRIEF DESCRIPTION OF CERTAIN EXAMPLE DRAWINGS

The drawings submitted herewith, which form a part of this patent application, each illustrate an embodiment, or one or more components of an embodiment, of a non-limiting example of applicants' invention. While these drawings depict certain preferred embodiments of applicants' invention, as well as certain particularly desirable features thereof, they are intended to be examples only and should not be construed to limit the scope of applicants' invention.

DETAILED DESCRIPTION OF CERTAIN EXAMPLE EMBODIMENTS OF THE INVENTION

For a more complete understanding of the present invention, reference is now made to the following description of various illustrative and non-limiting embodiments thereof, taken in conjunction with the accompanying drawings in which like reference numbers indicate like features. These example embodiments, disclosed and discussed below, will assist in a further understanding of the inventions described and claimed herein, but they are not intended to limit the scope of the invention in any way.

Figure 1A:
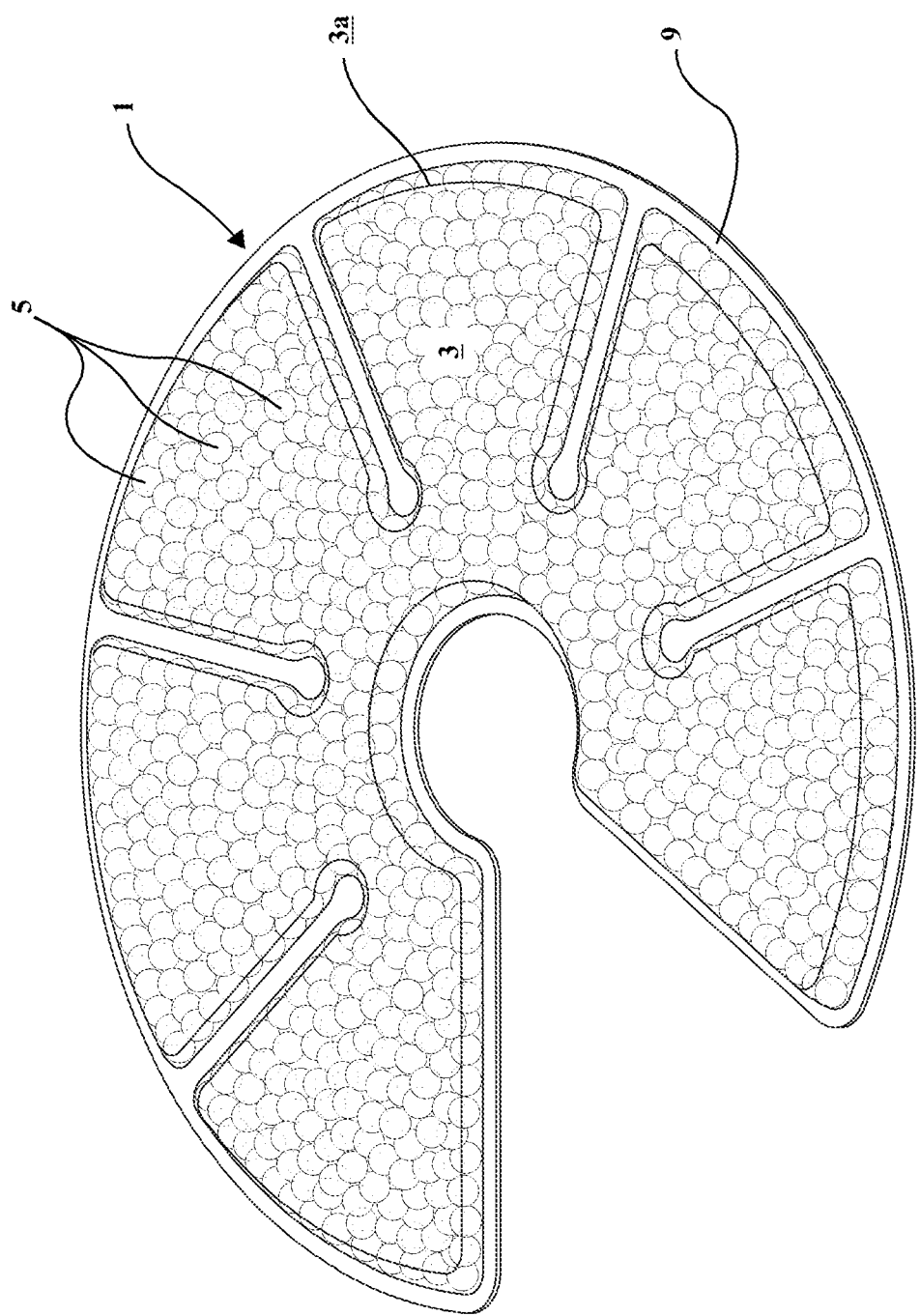
FIG. 1A illustrates one non-limiting embodiment of a temperature therapy pack according to the subject invention.
Figure 1B:
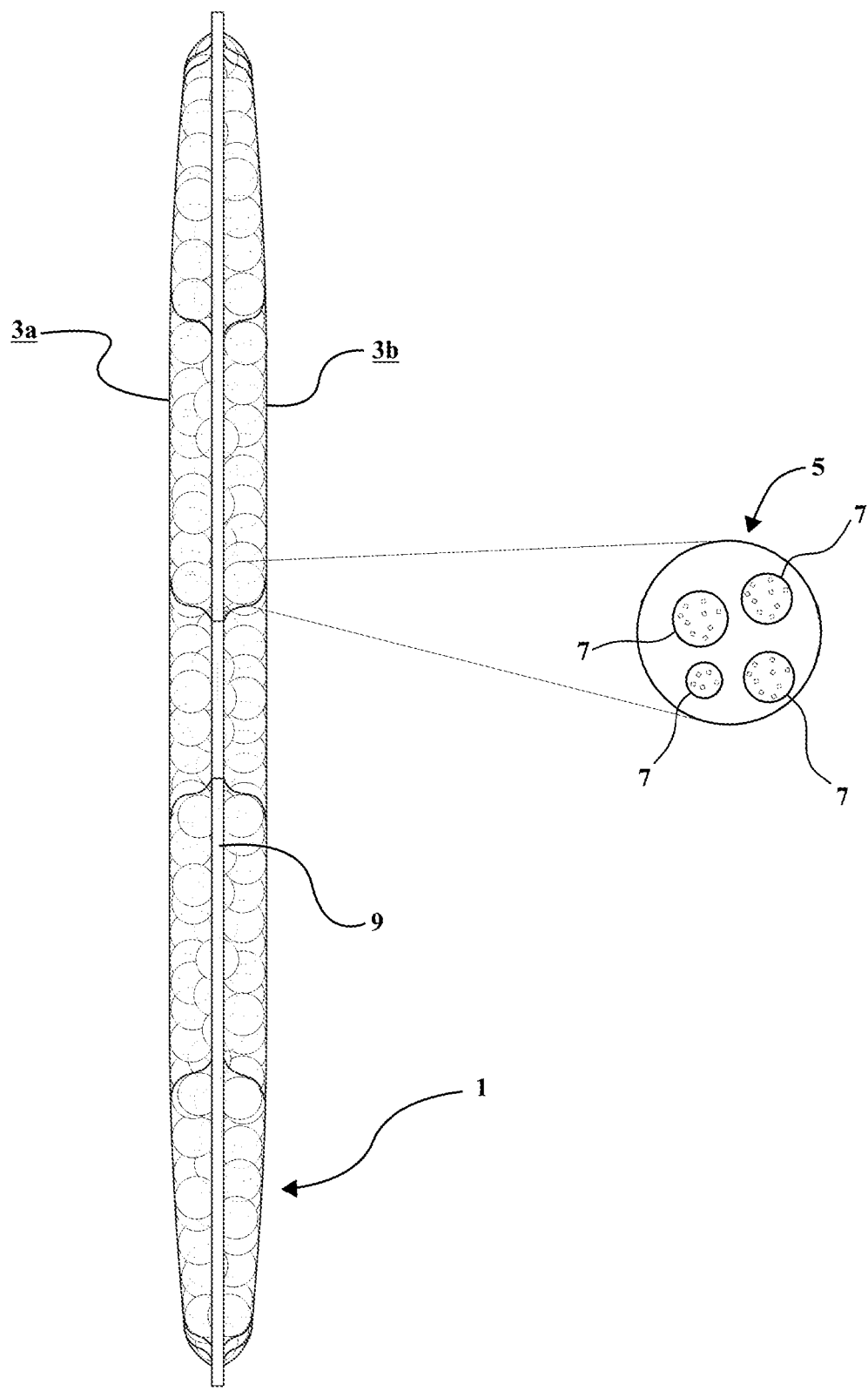
FIG. 1B illustrates an alternative view of the embodiment of the temperature therapy pack illustrated in FIG. 1A.

Referring initially to FIG. 1, one example embodiment of thermal pack in which the novel compositions described herein find utility is illustrated therein. As illustrated, thermal pack 1 is a therapy pack constructed of a pouch or pack shell 3 filled with a plurality spherical elements 5 which collectively comprise a temperature exchange material which can be heated or cooled for providing hot or cold temperature therapy to a user. More specifically, in the embodiment illustrated, the shell (or pouch) of the thermal pack is a polyvinyl chloride ("PVC") (front) sheet 3*a* formed into a desirable shape, such as the semi-circle pack configuration depicted in FIG. 1 (e.g., useful for treating mastitis), joined to a similarly shaped, second (rear) sheet 3*b* along the perimeter of each respective sheet. This is done preferably using heat or infrared welding, or using other suitable techniques such as adhesives, to form a sealed edge 9 as illustrated. Of course, the manner of connecting the sheets to form a pack is not material to the invention, and the pack may be assembled using different joining or construction methods. Similarly, the pack shell may be constructed from other materials such as (for example) polyethelene ("PE"), or from any other suitable material, or combination of materials. Suitable materials will preferably include one or more features of flexibility, durability when exposed to heat or cold (and/or to thermal cycling), and the ability to exhibit transparent or semi-transparent properties (i.e., visual transparency). Similarly, the pack need not be made from separate sheets but could be extruded or prepared using a single sheet folded over (and edge sealed), for example.

By joining only the edges or perimeter of the sheets, the sealed edge 9 is obtained while leaving the interior of the shell or pouch with a defined volume which is filled with the plurality of spherical elements 5, as illustrated. As described in further detail in conjunction with the examples provided below, spherical elements 5 are preferably semi-solid gel beads, formed from a polymeric hydrogel impregnated with thermochromic agents 7 (See FIG. 1B) in a novel process to obtain improved bead durability and improved thermochromic properties, including increased color-change functionality lifespan and increased numbers of color changing cycles (i.e., the product can change colors more times than prior art products).

As will be readily appreciated, because thermochromic hydrogel beads are utilized (in this embodiment), pack 1 is preferably constructed using a pack shell which is transparent, or which at least includes portions which are transparent, so that the color-changing properties of the beads within pack 1 can be viewed by the pack user. Thus, for example, the entire pack shell may be transparent or, alternatively, one side may be transparent with the other side being formed of an opaque fabric for comfort. Further alternatively, transparent windows may be provided in an otherwise opaque pack shell so that the thermochromic beads may be viewed by a user.

As discussed above, the preferred embodiments of the herein described inventions utilize thermochromic pigments incorporated into temperature therapy packs, so that the (approximate) temperature of the therapy pack can be readily ascertained by simply viewing the color of the pack itself. By incorporating thermochromic properties as such, by simply viewing the color of the therapy pack, it is possible to readily determine whether the pack is heated or cooled, and thus ready to provide temperature therapy. Moreover, it is possible to ascertain, simply by viewing the pack, which type of therapy the pack is ready to deliver. Nevertheless, it is always recommended to measure the temperature of the heated or cooled therapy pack prior to use (to verify that it is not too hot or too cold), to prevent burns or frost bite.

For heat treatments to be therapeutic, the temperature of the hot/cold pack should be at least several degrees Celsius above the skin temperature of a user. Similarly, for cold treatments to be therapeutic, the temperature of the hot/cold pack should be at least several degrees Celsius below the skin temperature of the user. Thus, for effective cold therapy, the temperature exchange material of a therapy pack (e.g., elements 5 of pack 1) should be cooled to a suitably cool temperature, such as by cooling the pack in a freezer (or using a cold water bath, or other suitable method). Conversely, for effective hot therapy, the temperature exchange material of a therapy pack should be heated to a suitably warm temperature, which may be accomplished by microwaving the pack (or using hot water, or other suitable method). Too high or too low temperatures should always be avoided for safety reasons. Therefore, the temperature of the pack should always be tested before use.

Recognizing that certain temperature ranges are desirable, preferred embodiments of the thermal packs described herein are configured so that color indicia are displayed when the temperature exchange material falls within such temperature ranges, and also so that separate color indicia is displayed when the temperature exchange material falls outside of those ranges. For example, in one particularly preferred embodiment, a pack is configured to include a temperature exchange material composition, which includes specifically selected thermochromic agents so that the exemplar thermal pack appears blue when at room (non-therapeutic) temperature, purple when it is cooled to the temperature range suitable for doctor recommended cold therapy, and white or clear when it is heated to the temperature range suitable for doctor recommended heat therapy. Of course, any temperature ranges described herein are not intended to be limiting, and the thermal packs described herein can be tailored to display such colors in different temperature ranges (or, in another example, to display different colors within the same ranges).

Generally speaking, thermochromic colorants function by selectively absorbing a portion of the visible spectrum of light, leaving the remaining portion of the spectrum to be reflected and thus observed. Thus, when thermochromic colorants are integrated into a thermal exchange material, such as a solid, semi-solid, or continuous gel, the apparent color of the gel, at a given temperature, will depend on the colors reflected (i.e., not absorbed) at the respective temperature. On this same point, it is important to note that thermochromic materials can be designed (or selected) so that they display color above or below threshold temperatures (i.e., develop or turn on), or de-color above or below threshold temperatures (i.e., turn off). For example, a red de-coloring thermochromic powder may display the color red at temperatures below 0° C., but display no color (i.e., be colorless) at temperatures above 0° C. Conversely, a red developing thermochromic powder may display no color (i.e., appear colorless) at temperatures below 50° C., but display the color red at temperatures above 50° C.

As one facet of the many improvements to the prior art described herein, applicants have discovered a composition and process to obtain a thermal pack product which visually indicates three temperature ranges, using only two thermochromic agents, thereby saving the costs of the use of a third thermochromic agent, while also obtaining a thermal exchange material, in gel form, which is more stable, and which exhibits improved reversible thermochromic performance. As one example of such an improved thermal exchange gel, the gel is formed from a particularly selected composition so that the gel appears blue at room temperature (between approximately 0 and 38 degrees Celsius), colorless/white above 38 degrees Celsius (e.g., at temperatures effective for heat therapy), and purple below 0 degrees Celsius (e.g., at temperatures effective for cold therapy). Such a product, as described in more full detail infra, utilizes the two thermochromic agents synergistically to create a third color, by reflecting two colors simultaneously (within a pre-selected temperature range), so that the spectrum of the two colors reflected blends visually thereby appearing as a third color. In this specific embodiment, for example, the thermochromic pigments are selected so that the first—in this case blue—thermochromic agent de-colors (absorbing all wavelengths to appear clear or white) above 38 degrees Celsius, while otherwise appearing blue at any temperature below 38 degrees Celsius. The second thermochromic agent—in this case red—normally appears white or clear at any temperature above 0 degrees Celsius but develops into the color red below such temperature. Consequently, in a temperature range where the blue thermochromic pigment has not de-colored (and therefore displays as blue) and the red thermochromic pigment has developed to display red—in this case the temperature range below 0 degrees Celsius—the reflected blue and red light spectrums combine and visually appear purple to a human eye.

As aforesaid, in the example embodiment illustrated, the exemplary product described displays three colors—white/colorless, blue, and purple—in three different temperature ranges, but using only two thermochromic pigments. The elimination, in this instance, of the use of a third thermochromic pigment (to obtain the third color) not only saves costs (i.e., thermochromic pigments are expensive) but also results in a more structurally stable, better performing color product, particularly when the utilized thermochromic pigments are blended as a powder with a grain size selected between approximately 5-20 micrometers. In such instance, the grain particle size contributes to this better performance, as does the use of less thermochromic pigment (the smaller amount of pigment thereby replacing less polymer, resulting in a stronger gel product).

In the embodiment described immediately above, the two thermochromic powders are blended with a polymer mixture which is further processed to form either a continuous gel or a plurality of semi-solid (or solid) hydrogel beads. In the example embodiment employing beads, the resulting gel bead product is then installed in a (preferably) transparent thermal pack shell, as the plurality of spherical elements 5, and thereafter serves the role of the temperature exchange material of the thermal pack depicted in FIG. 1. As such, because the thermochromic pigments are integrated into the temperature exchange material itself, the pack 1, in addition to the other advantages described herein, more accurately signals the true temperature of the therapy pack, as compared to if the thermochromic pigments were installed in the outer pack shell (the outer pack shell temperature being sensitive to ambient air, surfaces which it contacts, etc.).

Pack 1, as illustrated in FIG. 1, is designed and intended to be heated (e.g., in a microwave) and cooled (e.g., to freezing temperatures) through numerous heating and cooling cycles so that both hot and cold therapy can be delivered (in alternative or alternating therapy treatments) using the same therapy pack. Consequently, the novel thermochromic hydrogels described herein are constructed, from the herein described compositions using the herein described methods, such that they are capable of being heated and cooled repeatedly without loss of structural integrity of the hydrogel. Thus, in embodiments in which the hydrogels described herein are formed into (preferably deformable semi-solid) spherical beads, the heating and cooling cycles will not degrade the bead structure (i.e., beads will remain beads). Similarly, in embodiments which employ a continuous gel, the continuous gel will not be detrimentally impacted by the heating and cooling cycles. Likewise, the thermochromic agents used in the various embodiments described herein are impregnated within the hydrogel using compositions and methods that result in lasting integration and improved thermochromic (i.e., color changing) performance.

General Procedure:

Generally speaking, one method of preparing the thermochromic polymers, useful as thermal exchange materials, is performed using the following steps:

Step 1: Mix the dispersant, dispersing auxiliary, solvent, and thermochromic powder. Combine the pre-mixed thermochromic composition with the raw polymerization material obtained from the polyacrylic polymer (and/or cellulose derivative) to obtain a mixed liquid. Preferably maintain the pH of the mixed liquid between approximately 3-10.

Step 2: Initiate polymerization of the mixed liquid at 40-88° C., to obtain thermochromic hydrogel (to be used in continuous gel or microsphere form). Avoid high reaction temperatures which will damage or destroy the thermochromic powder (or its properties) or lead to colloidal implosion. Avoid too low reaction temperatures which will result in failure of polymerization.

In Step 2, if microspheres are being prepared, drip the mixed liquid during polymerization into an oil solution (e.g., silicone oil) in which beads will form. Afterwards, clean the microspheres (or beads) to remove the oil. The cleaning time is preferably approximately 10-30 minutes, and the cleaning temperature is preferably approximately 0-45° C. Afterwards, dry the microspheres at low temperature, preferably between 40-80° C., for approximately 1-4 hours. Applicant has discovered that it is necessary to avoid higher drying temperature ranges, because such higher drying temperatures damage the thermochromic pigments resulting in shorter pigment life and fewer available color change cycles. Conversely, applicant has discovered that drying with lower temperatures reduces process efficiency.

NON-LIMITING EXAMPLE EMBODIMENTS

Embodiment 1

This embodiment relates to a method for preparing a reversible thermochromic gel, comprising the following steps: premixing the thermochromic powder with dispersant, solvent and dispersing auxiliary to obtain thermochromic color paste, and mixing the thermochromic color paste with polymer to obtain a gel-form thermal exchange material. The specific components and their contents are as shown in Table 1.

TABLE 1

| Component | | Content/% |
|---|---|---|
| Polymer | Sodium polyacrylate | 40 |
| Thermochromic powder | 0° C. red decoloring type + 38° C. blue decoloring type, with the particle size of 5-10 μm | 1 |
| Dispersant | Tween-20 | 19 |
| Dispersing auxiliary | Allyl alcohol | 35 |
| Solvent | Glycerin | 5 |

The gel-form thermal exchange material prepared in the embodiment may be used in continuous gel form, or alternatively formed into gel microspheres (using steps described elsewhere in the specification). The thermal exchange gel is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Embodiment 2

This embodiment relates to a method for preparing a reversible thermochromic gel, comprising the following steps: premixing the thermochromic powder with dispersant, solvent, and dispersing auxiliary to obtain thermochromic color paste. The thermochromic color paste is thereafter mixed with polymer to obtain a gel-form thermal exchange material. The specific components and their contents are as shown in Table 2.

TABLE 2

| Component | | Content/% |
|---|---|---|
| Polymer | Ammonium alginate | 31 |
| Thermochromic powder | 0° C. blue decoloring type + 50° C. red developing type, with the particle size of 10-15 μm | 4.5 |
| Dispersant | Span-40 | 33 |
| Dispersing auxiliary | Butanetriol | 1.5 |
| Solvent | Propylene glycol | 30 |

The gel-form thermal exchange material prepared in the embodiment may be used in continuous gel form, or alternatively formed into gel microspheres (using steps described elsewhere in the specification). The thermal exchange gel is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Embodiment 3

This embodiment relates to a method for preparing a reversible thermochromic gel, comprising the following steps: premixing the thermochromic powder with dispersant, solvent, and dispersing auxiliary to obtain thermochromic color paste. The thermochromic color paste is thereafter mixed with polymer to obtain a gel-form thermal exchange material. The specific components and their contents are as shown in Table 3.

TABLE 3

| Component | | Content/% |
|---|---|---|
| Polymer | Sodium carboxymethyl cellulose | 25 |
| Thermochromic powder | 40° C. blue developing type + 55° C. red developing type, with the particle size of 15-20 μm | 5 |
| Dispersant | Span-40 | 20 |
| Dispersing auxiliary | Allyl alcohol | 20 |
| Solvent | Propylene glycol | 30 |

The gel-form thermal exchange material prepared in the embodiment may be used in continuous gel form, or alternatively formed into gel microspheres (or beads). Afterwards, the thermal exchange gel is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Embodiment 4

This embodiment relates to a method for preparing a plurality of reversible thermochromic microspheres, comprising the following steps:

Mixing the dispersant, dispersing auxiliary, solvent, and thermochromic powder, and thereafter adding such mixture to the polymerization raw material of the polyacrylic polymer (or mixed solution of monomer and initiator) to obtain a mixed liquid. Afterwards, the mixed liquid is dripped into an oil phase, to allow the polymerization reaction to form thermochromic microspheres. The polymerization temperature is preferably controlled to remain between 40° C.-88° C. Higher or lower temperatures can prevent formation of the microspheres. After completion of polymerization, clean the microspheres (or beads) to remove the oil. The cleaning time is preferably approximately 10-30 minutes, and the cleaning temperature is preferably approximately 0-45° C. Afterwards, dry the microspheres at low temperature, preferably between 40-80° C., for approximately 1-4 hours. Applicant has discovered that it is necessary to avoid higher drying temperature ranges, because such higher drying temperatures damage the thermochromic pigments resulting in shorter pigment life and fewer available color change cycles. Conversely, applicant has discovered that drying with lower temperatures reduces process efficiency. After cleaning and drying is complete, the plurality of microshperes obtained are useful as a thermal exchange material.

The specific components and their contents in the embodiment are as shown in Table 4.

TABLE 4

| Component | | Content/% |
| --- | --- | --- |
| Polymer | Polymethacrylate (The mass ratio of methacrylate to potassium persulfate is 50:1) | 38 |
| Thermochromic powder | −10° C. blue decoloring type + 38° C. red developing type + 55° C. yellow developing type, with the particle size of 15-20 μm | 7 |
| Dispersant | Span-80 | 1.5 |
| Dispersing auxiliary | Polyglycerol | 28.5 |
| Solvent | Propylene glycol | 25 |

After the gel-form, microsphere-configured thermal exchange materials are obtained, the thermal exchange material is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Embodiment 5

This embodiment relates to a method for preparing a reversible thermochromic gel, comprising the following steps:

Mixing the dispersant, dispersing auxiliary, solvent, and thermochromic powder, and thereafter adding such mixture to the polymerization raw material of the polyacrylic polymer (or mixed solution of monomer and initiator) to obtain a mixed liquid. Afterwards, the mixed liquid is directly polymerized between approximately 40-88° C. to obtain a continuous gel form thermal exchange material.

The specific components and their contents in the embodiment are as shown in Table 5.

TABLE 5

| Component | | Content/% |
| --- | --- | --- |
| Polymer | Sodium polyacrylate (The mass ratio of sodium acrylate to ammonium persulfate is 200:1) | 5 |
| Thermochromic powder | −10° C. blue decoloring type + 38° C. red developing type + 55° C. yellow developing type, with the particle size of 10-20 μm | 5 |
| Dispersant | Tween-80 | 30 |
| Dispersing auxiliary | N-propanol | 30 |
| Solvent | Water | 30 |

The gel-form thermal exchange material prepared in the embodiment is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Embodiment 6

This embodiment relates to a method for preparing a reversible thermochromic gel, comprising the following steps:

Premixing the thermochromic powder with dispersant, solvent, and dispersing auxiliary to obtain thermochromic color paste, and thereafter mixing the thermochromic color paste with polymer to obtain a gel-form thermal exchange material. The specific components and their contents are as shown in Table 6.

TABLE 6

| Component | | Content/% |
| --- | --- | --- |
| Polymer | Polyacrylamide | 20 |
| | Agar | 20 |
| Thermochromic powder | 0° C. red decoloring type + 38° C. blue decoloring type, with the particle size of 5-10 μm | 1 |
| Dispersant | Tween-20 | 19 |
| Dispersing auxiliary | Allyl alcohol | 35 |
| Solvent | Glycerin | 5 |

The gel-form thermal exchange material prepared in the embodiment may be used in continuous gel form, or alternatively formed into gel microspheres (or beads). Afterwards, the thermal exchange gel is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Embodiment 7

This embodiment relates to a method for preparing a reversible thermochromic gel, comprising the following steps:

Premixing the thermochromic powder with dispersant, solvent, and dispersing auxiliary to obtain thermochromic color paste, and thereafter mixing the thermochromic color paste with polymer to obtain a gel-form thermal exchange material. The specific components and their contents are as shown in Table 7.

TABLE 7

| Component | | Content/% |
|---|---|---|
| Polymer | Polyacrylamide | 20 |
| | Hydroxyethyl cellulose | 20 |
| Thermochromic powder | 0° C. red decoloring type + 38° C. blue decoloring type, with the particle size of 5-10 μm | 1 |
| Dispersant | Tween-20 | 19 |
| Dispersing auxiliary | Allyl alcohol | 35 |
| Solvent | Glycerin | 5 |

The gel-form thermal exchange material prepared in the embodiment may be used in continuous gel form, or alternatively formed into gel microspheres (or beads). Afterwards, the thermal exchange gel is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Embodiment 8

This embodiment relates to a method for preparing a reversible thermochromic gel, comprising the following steps:

Premixing the thermochromic powder with dispersant, solvent, and dispersing auxiliary to obtain thermochromic color paste, and thereafter mixing the thermochromic color paste with polymer to obtain a gel-form thermal exchange material. The specific components and their contents are as shown in Table 8.

TABLE 8

| Component | | Content/% |
|---|---|---|
| Polymer | Agar | 20 |
| | Hydroxyethyl cellulose | 20 |
| Thermochromic powder | 0° C. red decoloring type + 38° C. blue decoloring type, with the particle size of 5-10 μm | 1 |
| Dispersant | Tween-20 | 19 |
| Dispersing auxiliary | Allyl alcohol | 35 |
| Solvent | Glycerin | 5 |

The gel-form thermal exchange material prepared in the embodiment may be used in continuous gel form, or alternatively formed into gel microspheres (or beads). Afterwards, the thermal exchange gel is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Embodiment 9

This embodiment relates to a method for preparing a reversible thermochromic gel, comprising the following steps:

Premixing the thermochromic powder with dispersant, solvent, and dispersing auxiliary to obtain thermochromic color paste, and thereafter mixing the thermochromic color paste with polymer to obtain a gel-form thermal exchange material. The specific components and their contents are as shown in Table 9.

TABLE 9

| Component | | Content/% |
|---|---|---|
| Polymer | Polyacrylamide | 15 |
| | Hydroxyethyl cellulose | 12 |
| | Agar | 13 |
| Thermochromic powder | 0° C. red decoloring type + 38° C. blue decoloring type, with the particle size of 5-10 μm | 1 |
| Dispersant | Tween-20 | 19 |
| Dispersing auxiliary | Allyl alcohol | 35 |
| Solvent | Glycerin | 5 |

The gel-form thermal exchange material prepared in the embodiment may be used in continuous gel form, or alternatively formed into gel microspheres (or beads). Afterwards, the thermal exchange gel is preferably installed into a thermal pack shell, such as the exemplar shell depicted as 3 in FIG. 1. The result is a reversible thermochromic hot/cold therapy pack which can be used to provide hot and/or cold temperature therapy (e.g., by heating the obtained pack in a microwave, or cooling it in a freezer).

Comparative Example 1

The embodiment relates to a method for preparing a reversible thermochromic gel; the preparation steps are basically the same as that in Embodiment 1, except that: the content of sodium polyacrylate is 45% and the content of allyl alcohol is 30%.

Comparative Example 2

The embodiment relates to a method for preparing a reversible thermochromic gel; the preparation steps are basically the same as that in Embodiment 1, except that: the content of thermochromic powder is 0.5% and the content of allyl alcohol is 34.5%.

Comparative Example 3

The embodiment relates to a method for preparing a reversible thermochromic gel; the preparation steps are basically the same as that in Embodiment 1, except that: the dispersing auxiliary is ethylene glycol.

Comparative Example 4

The embodiment relates to a method for preparing a reversible thermochromic gel; the preparation steps are basically the same as that in Embodiment 1, except that: the solvent is methanol.

Comparative Example 5

The embodiment relates to a method for preparing a reversible thermochromic gel; the preparation steps are basically the same as that in Embodiment 1, except that: the particle size of thermochromic powder is 25 microns.

Comparative Example 6

The embodiment relates to a method for preparing a reversible thermochromic microsphere; the preparation steps are basically the same as that in Embodiment 3, except that: the polymerization temperature is controlled at 100° C.

Comparative Example 7

The embodiment relates to a method for preparing a reversible thermochromic microsphere; the preparation steps are basically the same as that in Embodiment 3, except that: the cleaning temperature of the thermochromic microsphere is controlled at 50° C.

Performance Test

The 50° C. accelerated aging test method was used to test the storage life, and to simulate the actual use conditions, in order to approximate the times for which the color change performance of the product will be available. That is, in addition to testing the product for a sufficiently long shelf-life prior to use, the tests performed were designed to determine when or whether the thermochromic pigments will lose performance, upon being subjected to hot and cold thermal cycling (e.g., heating and freezing). The tests were performed for the thermochromic product prepared in each embodiment described above. The test results are as shown in Table 10 below:

TABLE 10

|   | Thermochromic range | Color change cycles available (estimated) | Storage life (Months-estimated) | Discoloration condition/color retention properties |
|---|---|---|---|---|
| Embodiment 1 | Being purple below 0° C., blue within 0° C.-38° C., and colorless above 38° C. | 255 | 36 | Retains color well |
| Embodiment 2 | Being blue below 0° C., colorless within 0° C.-50° C., and red above 50° C. | 260 | 37 | Retains color well |
| Embodiment 3 | Being colorless below 40° C., blue within 40° C.-55° C., and purple above 55° C. | 264 | 37 | Retains color well |
| Embodiment 4 | Being blue below −10° C., colorless within −10° C.-38° C., red within 38° C.-55° C., and orange above 55° C. | 257 | 36 | Retains color well |
| Embodiment 5 | Being blue below −10° C., colorless within −10° C.-38° C., red within 38° C.-55° C., and orange above 55° C. | 265 | 37 | Retains color well |
| Embodiment 6 | Being purple below 0° C., blue within 0° C.-38° C., and colorless above 38° C. | 258 | 36 | Retains color well |
| Embodiment 7 | Being purple below 0° C., blue within 0° C.-38° C., and colorless above 38° C. | 280 | 39 | Retains color well |
| Embodiment 8 | Being purple below 0° C., blue within 0° C.-38° C., and colorless above 38° C. | 260 | 36 | Retains color well |
| Embodiment 9 | Being purple below 0° C., blue within 0° C.-38° C., and colorless above 38° C. | 262 | 36 | Retains color well |
| Comparative example 1 | Being purple below 0° C., blue within 0° C.-38° C., and colorless above 38° C. | 77 | 11 | Easy to discolor |
| Comparative example 2 | Being purple below 0° C., blue within 0° C.-38° C., and colorless above 38° C. | 56 | 9 | Easy to discolor |
| Comparative example 3 | Being purple below 0° C., blue within 0° C.-38° C., and colorless above 38° C. | 60 | 7 | Easy to discolor |
| Comparative example 4 | Being purple below 0° C., blue within 0° C.-38° C., and colorless above 38° C. | 33 | 5 | Easy to discolor |
| Comparative example 5 | Being purple below 0° C., blue within 0° C.-38° C., and colorless above 38° C. | 85 | 10 | Easy to discolor |
| Comparative example 6 | Being blue below −10° C., colorless within −10° C.-38° C., red within 38° C.-55° C., and orange above 55° C. | 40 | 6 | Easy to discolor |
| Comparative example 7 | Being blue below −10° C., colorless within −10° C.-38° C., red within 38° C.-55° C., and orange above 55° C. | 63 | 9 | Easy to discolor |

Figure 2:
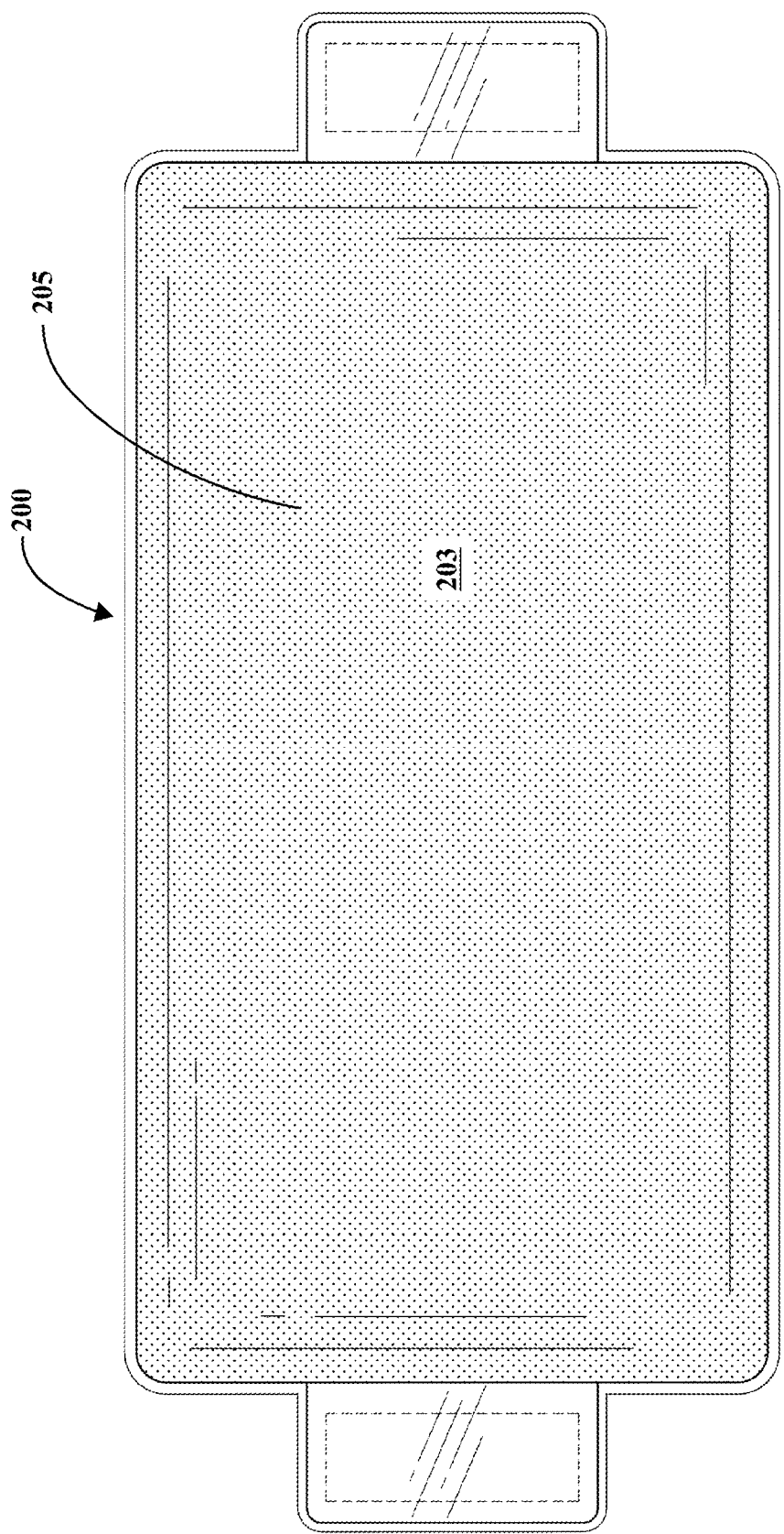
FIG. 2 illustrates an alternative embodiment of a temperature therapy pack according to the subject invention.
Figure 3:
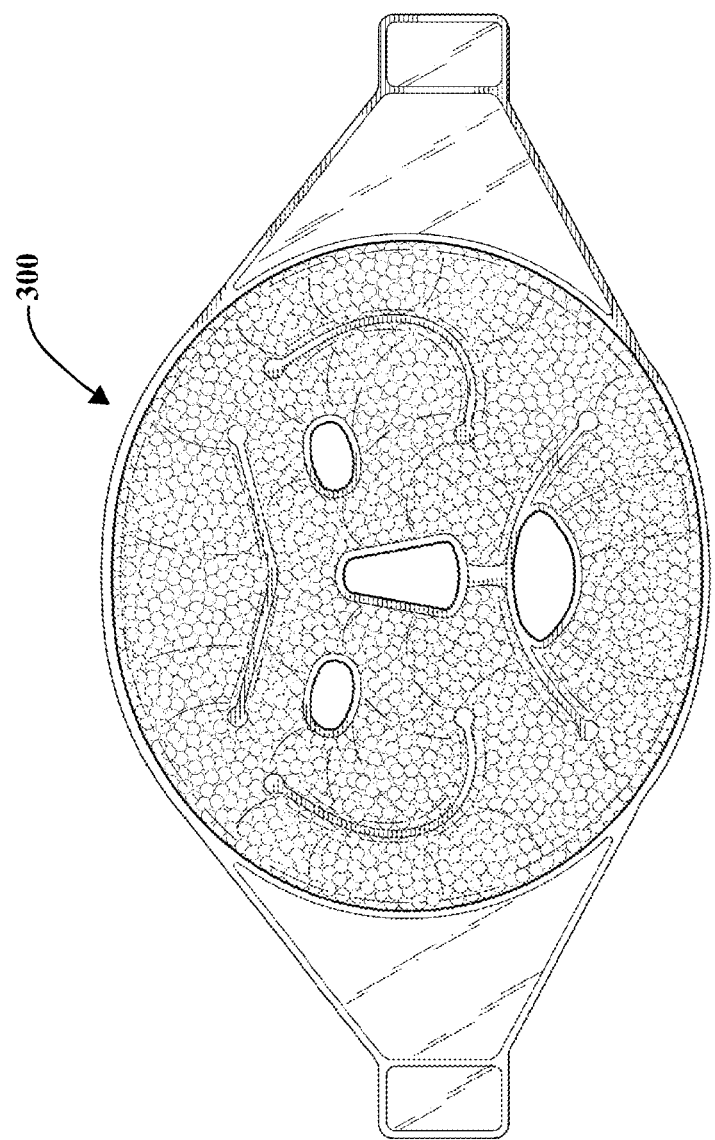
FIG. 3 illustrates an alternative embodiment of a temperature therapy pack according to the subject invention.
Figure 4:
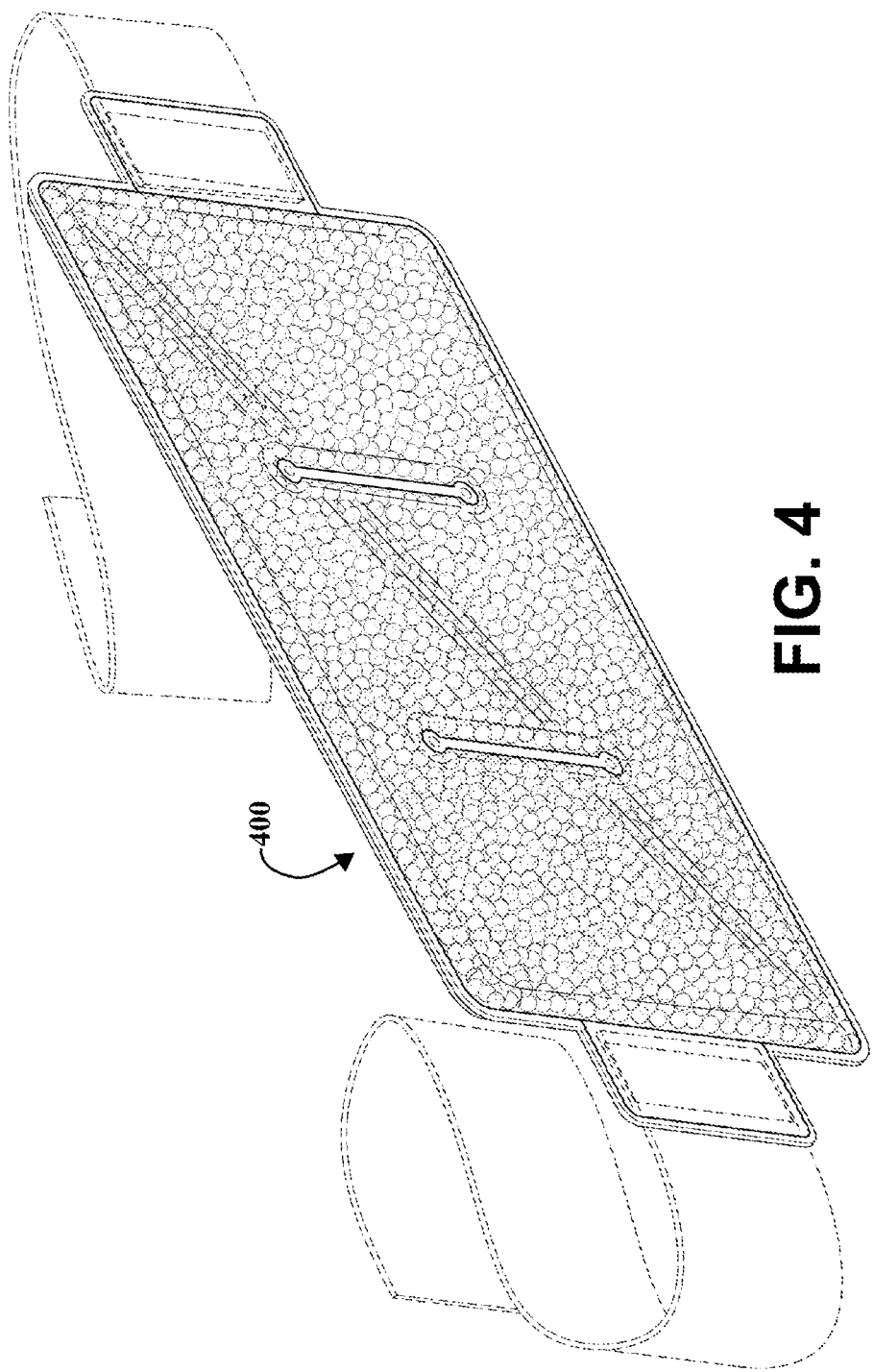
FIG. 4 illustrates an alternative embodiment of a temperature therapy pack according to the subject invention.
Figure 5:
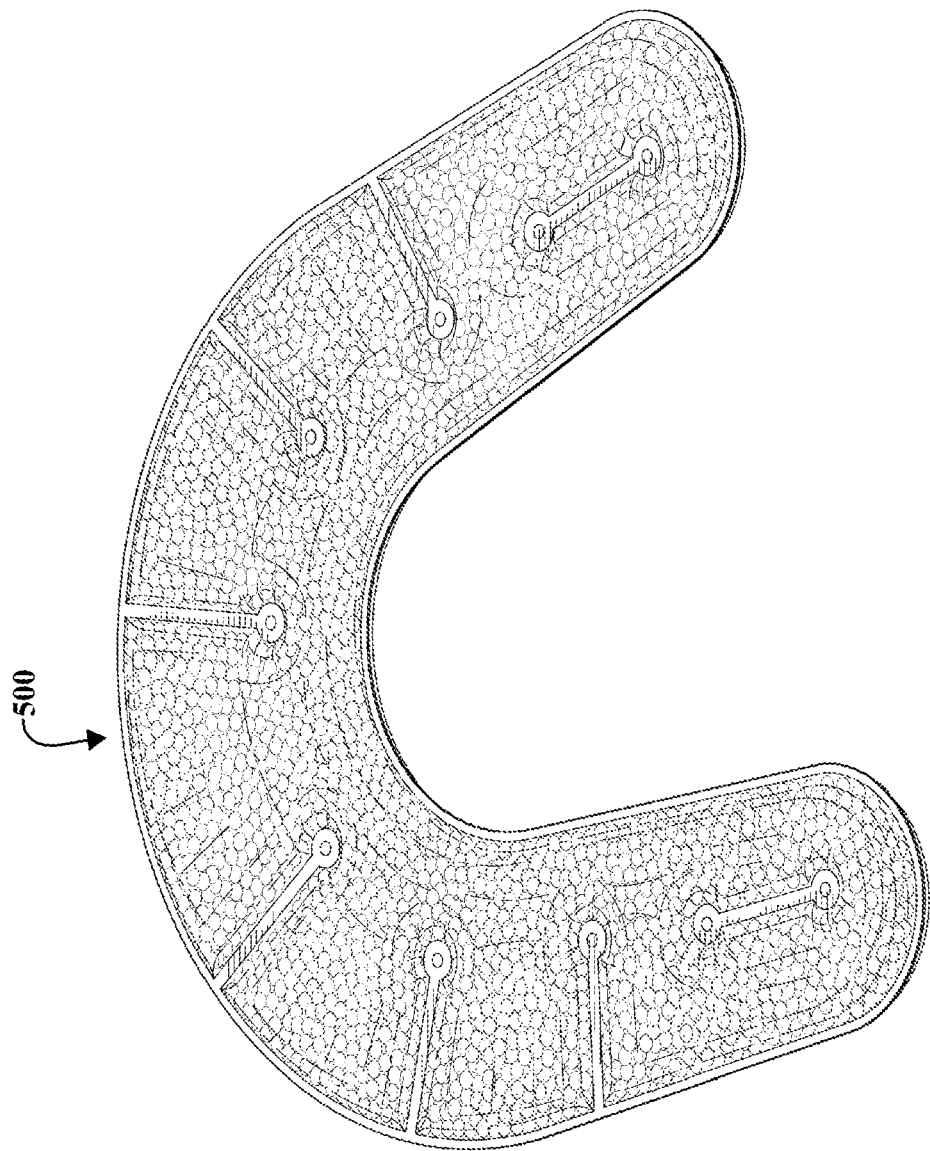
FIG. 5 illustrates an alternative embodiment of a temperature therapy pack according to the subject invention.
Figure 6:
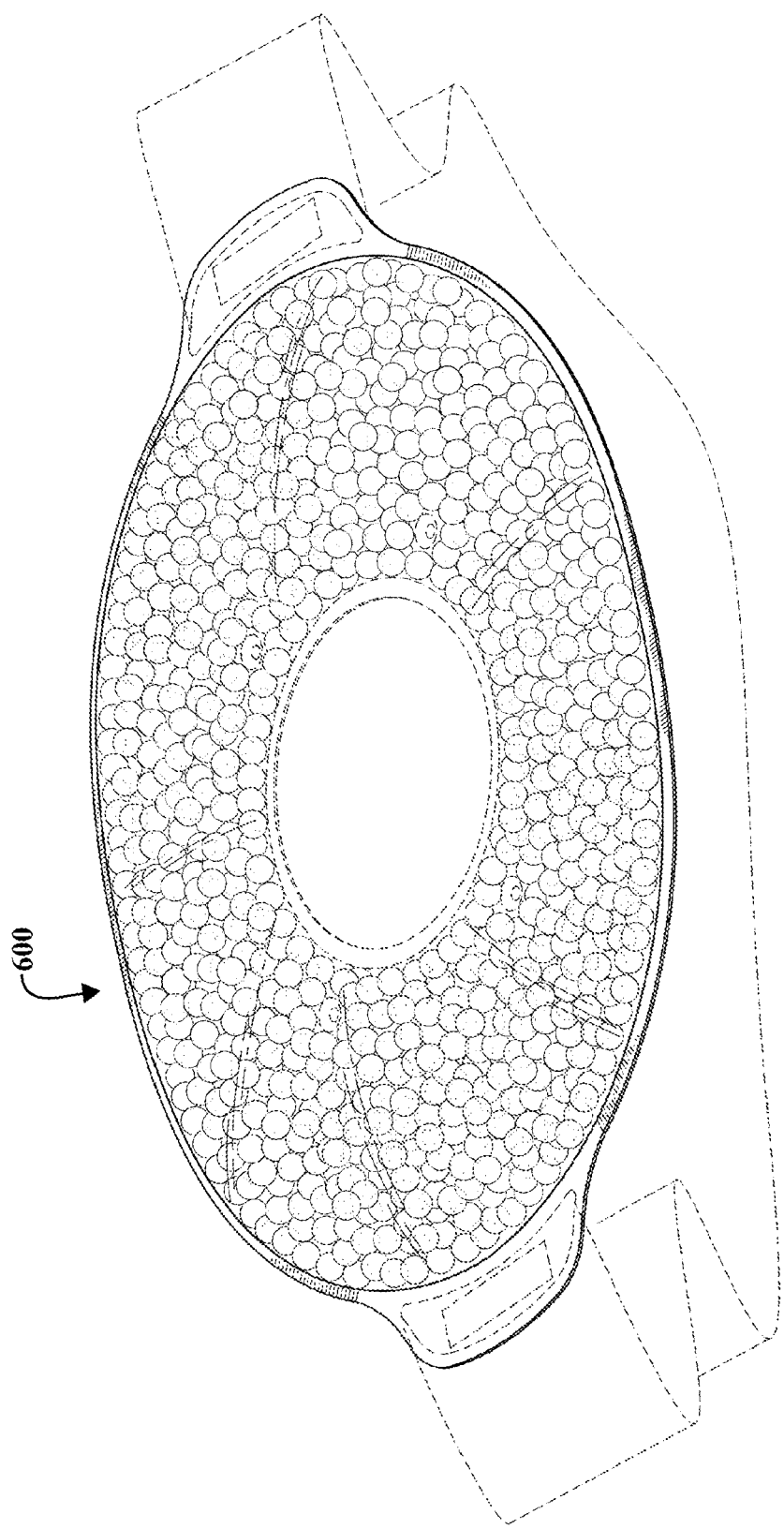
FIG. 6 illustrates an alternative embodiment of a temperature therapy pack according to the subject invention.

Although the above disclosed thermal pack embodiments have generally been discussed in connection with FIG. 1, which illustrates hydrogel thermal exchange material formed into beads or microspheres (i.e., as spherical elements 5), continuous gel embodiments, such as the example thermal pack 200 illustrated in FIG. 2, are also contemplated within the scope of the invention. Thermal pack 200, like thermal pack 1, utilizes a hydrogel thermal exchange material, but in continuous or fluid-like gel form 205, also impregnated with reversible thermochromic pigment (to obtain the functionalities and improvements described herein) (not shown). Moreover, the shell 203 of thermal pack 200, like thermal pack 1, may be formed in an unlimited number of ways without departing from the scope of the invention (e.g., with IR welding, extrusion, etc.). Further, in some preferred embodiments, ultraviolet coatings or filtering layers are applied (in this or other embodiments) on the transparent thermal pack shell (or elsewhere).

In optional embodiments of the thermal packs enabled by this specification, the thermal packs may be configured and shaped to conform to specific human body parts. For example, FIGS. 3-6 depict packs shaped to conform to the face (pack 300), back (pack 400), neck (pack 500), and knee (pack 600), respectively. Any other shape of pack may, of course, be utilized. Most preferably, continuous gel thermal packs will utilize gel compositions which do not freeze, and therefore remain soft and pliable, even when cooled to below 0 degrees Celsius. Similarly, in embodiments such as pack 1 (see FIG. 1) which utilize microspheres or beads as the thermal exchange material, it is preferred to use at least a small amount of liquid, to lubricate and enable bead movement and flow, which also includes an anti-freeze agent to prevent solidification of the pack when cooled to freezing temperatures (to maintain comfort in use). Suitable example antifreeze additives which may be used are propylene glycol, glycerin, and others.

In certain example embodiments, the percentage of hydrogel beads within the pack volume may range from 10% to 100%, including between 20% to 80% and between 40% to 60% with the balance of the volume, if any, comprising liquid and/or air. Moreover, the hydrogel beads may all be solid, or they may be a combination of solid and hollow beads to enable tailoring of thermal exchange properties.

In addition to the advantages already described above, the following additional advantages of the herein described inventions are obtained alone, or in combination, with one or more of the above-described embodiments:

By selecting different polymer components and controlling the production process parameters, improved storage life and usage times of the products are obtained. Testing simulating product use suggests that storage life can reach more than 36 months and that usage can surpass more than 250 color changing cycles.

The polymer of the disclosure is preferably a mixture of polyacrylic polymer and cellulose derivative. Since the polyacrylic polymer has a gelling effect and the cellulose derivative has a thickening effect, the strength of the colloid is significantly enhanced through the synergistic effect between them, so that increased microsphere durability is obtained and the storage life of the gel can be prolonged.

Compared to prior art processing temperatures, the disclosure adopts a 40-88° C. polymerization condition, which obtains increased thermochromic pigment performance and durability, and results in high quality polymerization (e.g., resulting in longer storage life in use).

Compared to prior art drying temperatures, the disclosure adopts a 40-80° C. drying condition, which synergistically with the polymerization conditions used (described above), obtains further increased thermochromic pigment performance and durability. Moreover, the gel products obtained exhibit improved durability and mildew resistance, thereby improving the storage life and storage quality.

Once given the above disclosure, many other features, modifications, and improvements will become apparent to the skilled artisan. Such features, modifications, and improvements are therefore considered to be part of this invention, without limitation imposed by the example embodiments described herein. Moreover, any word, term, phrase, feature, example, embodiment, or part or combination thereof, as used to describe or exemplify embodiments herein, unless unequivocally set forth as expressly uniquely defined or otherwise unequivocally set forth as limiting, is not intended to impart a narrowing scope to the invention in contravention of the ordinary meaning of the claim terms by which the scope of the patent property rights shall otherwise be determined:

The invention claimed is:

1. A temperature therapy pack for providing hot and cold temperature therapy to a body part, and which displays color to indicate different therapy pack temperatures, comprising:
   a visually transparent temperature therapy pack enclosure;
   one or more thermochromic agents;
   a pack fill material comprising one or more gels, said pack fill material being combined with said one or more thermochromic agents to collectively comprise a reversible thermochromic, thermal exchange material, said reversible thermochromic, thermal exchange material being enclosed in said visually transparent temperature therapy pack enclosure;
   said reversible thermochromic, thermal exchange material being so compositionally, chemically configured such that it is capable of being alternately heated and cooled to provide heat or cold therapy, while remaining dimensionally stable;
   said reversible thermochromic, thermal exchange material comprises a hydrogel formed into a plurality of structurally durable beads;
   said temperature therapy pack being so configured such that when it is heated or cooled, said reversible thermochromic, thermal exchange material retains heat or cold, respectively, so that said temperature therapy pack can be applied to a body part of a user to provide hot or cold temperature therapy; and
   wherein said reversible thermochromic, thermal exchange material is so compositionally, chemically configured such as to:
   display a first color within a temperature range T1 inclusive of room temperature;
   display a second color within a temperature range T2, which is above said temperature range T1 and which is therapeutically suitable to provide heat therapy; and
   display a third color within a temperature range T3, which is below said temperature range T1 and which is therapeutically suitable to provide cold therapy;
   wherein said beads include, as said one or more thermochromic agents, one or more thermochromic pigments having a particle size selected from between approximately 5-20 micrometers; and
   wherein said reversible thermochromic, thermal exchange material comprises, by mass fraction:
   a polymer in the amount of 5%-40%;
   a thermochromic powder in the amount of 1%-7%;
   a dispersing agent in the amount of 1.5%-33%;
   a dispersing auxiliary in the amount of 1.5%-35%;
   a solvent in the amount of 5%-30%; and
   wherein said polymer comprises at least one of a polyacrylic acid polymer, a natural polymer, and a cellulose derivative.

2. A temperature therapy pack according to claim 1 wherein said hydrogel is comprised of a composition such that it is capable of being heated and cooled in repeat cycles, without substantial loss of structural integrity of the hydrogel.

3. A temperature therapy pack according to claim 1 wherein said pack is so configured such that a thermochromic display of said first, second, or third colors accurately signals a temperature of the therapeutically useful portions of said temperature therapy pack because said one or more thermochromic agents are located mixed within said reversible thermochromic, thermal exchange material, on the interior of said visually transparent temperature therapy pack enclosure.

4. A temperature therapy pack according to claim 1 wherein said reversible thermochromic, thermal exchange material includes only two thermochromic agents, but wherein said temperature therapy pack is capable of displaying at least three colors within said temperature ranges T1, T2, and T3 respectively, by spectrally combining first and second colors displayed by said two thermochromic agents, to obtain a third color in at least one said temperature range.

5. A temperature therapy pack according to claim 4 wherein the composition of said reversible thermochromic, thermal exchange material as having only two thermochromic agents, as compared to three or more thermochromic agents, results in a reduction of the mass percentage of thermochromic agent material, relative to gel material, resulting in more structurally stable, durable pack fill.

6. A temperature therapy pack for providing hot and cold temperature therapy to a body part, and which displays color to indicate different therapy pack temperatures, comprising:
a visually transparent temperature therapy pack enclosure;
one or more thermochromic agents;
a pack fill material comprising one or more gels, said pack fill material being combined with said one or more thermochromic agents to collectively comprise a reversible thermochromic, thermal exchange material, said reversible thermochromic, thermal exchange material being enclosed in said visually transparent temperature therapy pack enclosure;
said reversible thermochromic, thermal exchange material being so compositionally, chemically configured such that it is capable of being alternately heated and cooled to provide heat or cold therapy, while remaining dimensionally stable;
said reversible thermochromic, thermal exchange material comprises a hydrogel formed into a plurality of structurally durable beads;
said temperature therapy pack being so configured such that when it is heated or cooled, said reversible thermochromic, thermal exchange material retains heat or cold, respectively, so that said temperature therapy pack can be applied to a body part of a user to provide hot or cold temperature therapy; and
wherein said reversible thermochromic, thermal exchange material is so compositionally, chemically configured such as to:
display a first color within a temperature range T1 inclusive of room temperature;
display a second color within a temperature range T2, which is above said temperature range T1 and which is therapeutically suitable to provide heat therapy; and
display a third color within a temperature range T3, which is below said temperature range T1 and which is therapeutically suitable to provide cold therapy;
wherein said one or more thermochromic agents comprise:
a first thermochromic agent having properties selected to display a first color X within a baseline temperature range T1 inclusive of room temperature, which de-colors above a temperature T2; and
a second thermochromic agent having properties selected to display a second color Y below a temperature T3 which is below said baseline temperature range T1, which de-colors above said temperature T3, wherein when said reversible thermochromic, thermal exchange material of said temperature therapy pack is measurable at a temperature within said temperature range T1, said temperature therapy pack displays said first color X; when said thermal exchange material of said temperature therapy pack is measurable at a temperature above said temperature T2, said first and said second thermochromic agents each de-color; and when said thermal exchange material of said temperature therapy pack is measurable at a temperature below said temperature T3, said first color X and said second color Y, of said first and second thermochromic agents, respectively, each simultaneously display and thereby spectrally combine such that said temperature therapy pack displays a third color Z, which is a result of the spectral combination of colors X and Y; and
wherein said reversible thermochromic, thermal exchange material comprises, by mass fraction:
a polymer in the amount of approximately 5%-40%;
said first thermochromic agent in the amount of approximately 1%-3.5%;
said second thermochromic agent in the amount of approximately 1%-3.5%;
a dispersing agent in the amount of approximately 1.5%-33%;
a dispersing auxiliary in the amount of approximately 1.5%-35%;
a solvent in the amount of approximately 5%-30%; and
wherein said polymer comprises at least one of a polyacrylic acid polymer, a natural polymer, and a cellulose derivative.

7. A temperature therapy pack for providing hot and cold temperature therapy to a body part, and which displays color to indicate different therapy pack temperatures, comprising:
a visually transparent temperature therapy pack enclosure;
one or more thermochromic agents;
a pack fill material comprising one or more gels, said pack fill material being combined with said one or more thermochromic agents to collectively comprise a reversible thermochromic, thermal exchange material, said reversible thermochromic, thermal exchange material being enclosed in said visually transparent temperature therapy pack enclosure;
said reversible thermochromic, thermal exchange material being so compositionally, chemically configured such that it is capable of being alternately heated and cooled to provide heat or cold therapy, while remaining dimensionally stable;
said temperature therapy pack being so configured such that when it is heated or cooled, said reversible thermochromic, thermal exchange material retains heat or cold, respectively, so that said temperature therapy pack can be applied to a body part of a user to provide hot or cold temperature therapy; and
wherein said reversible thermochromic, thermal exchange material is so compositionally, chemically configured such as to:
display a first color within a temperature range T1 inclusive of room temperature;
display a second color within a temperature range T2, which is above said temperature range T1 and which is therapeutically suitable to provide heat therapy; and
display a third color within a temperature range T3, which is below said temperature range T1 and which is therapeutically suitable to provide cold therapy;
wherein said one or more thermochromic agents comprise:
a first thermochromic agent having properties selected to display a first color X within a baseline temperature range T1 inclusive of room temperature, which de-colors above a temperature T2; and
a second thermochromic agent having properties selected to display a second color Y below a temperature T3 which is below said baseline temperature range T1, which de-colors above said temperature T3, wherein when said reversible thermochromic, thermal exchange material of said temperature therapy pack is measurable at a temperature within said temperature range T1, said temperature therapy pack displays said first color X; when said thermal exchange material of said temperature therapy pack is measurable at a temperature above said temperature T2, said first and said second thermochromic agents each de-color; and when said thermal exchange material of said temperature therapy pack is measurable at a temperature below said temperature T3, said first color X and said second color Y, of said first and second thermochromic agents, respectively, each simultaneously display and thereby spectrally combine such that said temperature therapy pack displays a third color Z, which is a result of the spectral combination of colors X and Y; and wherein said reversible thermochromic, thermal exchange material comprises a polymer comprising at least one of polyacrylic acid, sodium polyacrylate, polyacrylamide, and acrylamide/sodium acrylate copolymer, and wherein the raw materials for the polymerization of polyacrylic polymer comprise a monomer and an initiator; the monomer comprises one or more of acrylic acid and the relevant acrylate, acrylamide and acrylic ester; the initiator comprises one or more of potassium persulfate, ammonium persulfate, tert-butyl hyperoxide and dimethyl sulfonyl peroxide; and the mass ratio of the monomer to initiator is about 50:1 to 200:1; and wherein said reversible thermochromic, thermal exchange material comprises, by mass fraction:

said polymer in the amount of approximately 5%-40%;

said first thermochromic agent in the amount of approximately 1%-3.5%;

said second thermochromic agent in the amount of approximately 1%-3.5%;

a dispersing agent in the amount of approximately 1.5%-33%;

a dispersing auxiliary in the amount of approximately 1.5%-35%; and a solvent in the amount of approximately 5%-30%.

8. A temperature therapy pack for providing hot and cold temperature therapy to a body part, and which displays color to indicate different therapy pack temperatures, comprising:

a visually transparent temperature therapy pack enclosure;

one or more thermochromic agents;

a pack fill material comprising one or more gels, said pack fill material being combined with said one or more thermochromic agents to collectively comprise a reversible thermochromic, thermal exchange material, said reversible thermochromic, thermal exchange material being enclosed in said visually transparent temperature therapy pack enclosure;

said reversible thermochromic, thermal exchange material being so compositionally, chemically configured such that it is capable of being alternately heated and cooled to provide heat or cold therapy, while remaining dimensionally stable;

said temperature therapy pack being so configured such that when it is heated or cooled, said reversible thermochromic, thermal exchange material retains heat or cold, respectively, so that said temperature therapy pack can be applied to a body part of a user to provide hot or cold temperature therapy; and wherein said reversible thermochromic, thermal exchange material is so compositionally, chemically configured such as to:

display a first color within a temperature range T1 inclusive of room temperature;

display a second color within a temperature range T2, which is above said temperature range T1 and which is therapeutically suitable to provide heat therapy; and display a third color within a temperature range T3, which is below said temperature range T1 and which is therapeutically suitable to provide cold therapy;

wherein said one or more thermochromic agents comprise:

a first thermochromic agent having properties selected to display a first color X within a baseline temperature range T1 inclusive of room temperature, which de-colors above a temperature T2; and a second thermochromic agent having properties selected to display a second color Y below a temperature T3 which is below said baseline temperature range T1, which de-colors above said temperature T3, wherein when said reversible thermochromic, thermal exchange material of said temperature therapy pack is measurable at a temperature within said temperature range T1, said temperature therapy pack displays said first color X; when said thermal exchange material of said temperature therapy pack is measurable at a temperature above said temperature T2, said first and said second thermochromic agents each de-color; and when said thermal exchange material of said temperature therapy pack is measurable at a temperature below said temperature T3, said first color X and said second color Y, of said first and second thermochromic agents, respectively, each simultaneously display and thereby spectrally combine such that said temperature therapy pack displays a third color Z, which is a result of the spectral combination of colors X and Y; and wherein said reversible thermochromic, thermal exchange material comprises a polymer comprising a natural polymer and said natural polymer is at least one selected from the group consisting of: agar, ammonium alginate, algin, alginic acid, amylopectin, gum tragacanth, calcium alginate, carrageenan, cassia gum, locust bean gum, quinoa starch, Guar gum, dehydroxanthan gum, dextrin, carrageenin, gelatin, Gellan gum, Ghatti gum, magnesium alginate, Natto gum, pectin, potassium alginate, potassium carrageenan, peach gum, Rhizobian gum, Sclerotium gum, sodium carrageenan, karaya gum, Tamarindus Indica seed gum, tapioca starch, TEA-alginate, Welan gum and Xathan gum; and wherein said reversible thermochromic, thermal exchange material comprises, by mass fraction:

said polymer in the amount of approximately 5%-40%;

said first thermochromic agent in the amount of approximately 1%-3.5%;

said second thermochromic agent in the amount of approximately 1%-3.5%;

a dispersing agent in the amount of approximately 1.5%-33%;

a dispersing auxiliary in the amount of approximately 1.5%-35%; and a solvent in the amount of approximately 5%-30%.

9. A temperature therapy pack for providing hot and cold temperature therapy to a body part, and which displays color to indicate different therapy pack temperatures, comprising:

a visually transparent temperature therapy pack enclosure;

one or more thermochromic agents;

a pack fill material comprising one or more gels, said pack fill material being combined with said one or more thermochromic agents to collectively comprise a reversible thermochromic, thermal exchange material, said reversible thermochromic, thermal exchange material being enclosed in said visually transparent temperature therapy pack enclosure;

said reversible thermochromic, thermal exchange material being so compositionally, chemically configured such that it is capable of being alternately heated and cooled to provide heat or cold therapy, while remaining dimensionally stable;

said temperature therapy pack being so configured such that when it is heated or cooled, said reversible thermochromic, thermal exchange material retains heat or cold, respectively, so that said temperature therapy pack can be applied to a body part of a user to provide hot or cold temperature therapy; and wherein said reversible thermochromic, thermal exchange material is so compositionally, chemically configured such as to:

display a first color within a temperature range T1 inclusive of room temperature;

display a second color within a temperature range T2, which is above said temperature range T1 and which is therapeutically suitable to provide heat therapy; and display a third color within a temperature range T3, which is below said temperature range T1 and which is therapeutically suitable to provide cold therapy;

wherein said one or more thermochromic agents comprise:

a first thermochromic agent having properties selected to display a first color X within a baseline temperature range T1 inclusive of room temperature, which de-colors above a temperature T2; and a second thermochromic agent having properties selected to display a second color Y below a temperature T3 which is below said baseline temperature range T1, which de-colors above said temperature T3, wherein when said reversible thermochromic, thermal exchange material of said temperature therapy pack is measurable at a temperature within said temperature range T1, said temperature therapy pack displays said first color X; when said thermal exchange material of said temperature therapy pack is measurable at a temperature above said temperature T2, said first and said second thermochromic agents each de-color; and when said thermal exchange material of said temperature therapy pack is measurable at a temperature below said temperature T3, said first color X and said second color Y, of said first and second thermochromic agents, respectively, each simultaneously display and thereby spectrally combine such that said temperature therapy pack displays a third color Z, which is a result of the spectral combination of colors X and Y; and wherein said reversible thermochromic, thermal exchange material comprises a polymer comprising a cellulose derivative and said cellulose derivative is at least one selected from the group consisting of: oxyhydroxypropyl cetyl hydroxyethylcellulose, calcium carboxymethyl cellulose, C12-16 alkyl PEG-2 hydroxypropyl hydroxyethyl ethylcellulose, carboxymethyl cellulose acetate butyrate, carboxymethyl hydroxyethyl cellulose, cellulase, cellulose acetate propionate, ascorbyl methylsilanol pectinate, calcium octenyl succinate starch, glyceryl alginate, hydrolyzed cellulose gum, hydroxyethyl chitosan, hydroxypropyl chitosan, hydroxypropyl guar gum, hydroxypropyl starch, hydroxypropyl starch phosphate, hydroxypropyl xanthan gum, carboxymethyl chitin, carboxymethyl chitosan, sodium carboxymethyl chitosan, sodium carboxymethyl dextrin, sodium polygluconate, sodium carboxymethyl starch, carboxymethyl glucosan, sodium starch octenyl succinate, starch hydroxypropyl trimethyl ammonium chloride, hexadecyl hydroxyethyl cellulose, croscarmellose, carboxymethyl hydroxypropyl guar gum, ethyl cellulose, sodium carboxymethyl cellulose, hydrogenated tallow benzyl dimethyl bentonite, hydroxybutyl methyl cellulose, hydroxyethyl cellulose, hydroxypropyl cellulose, hydroxypropyl methylcellulose, methyl cellulose, methyl ethyl cellulose, methyl hydroxyethyl cellulose, microcrystalline cellulose, nonylphenol polyether hydroxyethyl cellulose, oxycellulose, sodium cellulose sulfate and stearoxy PG-hydroxyethylcellulose sulfonate; and wherein said reversible thermochromic, thermal exchange material comprises, by mass fraction:

said polymer in the amount of approximately 5%-40%;

said first thermochromic agent in the amount of approximately 1%-3.5%;

said second thermochromic agent in the amount of approximately 1%-3.5%;

a dispersing agent in the amount of approximately 1.5%-33%;

a dispersing auxiliary in the amount of approximately 1.5%-35%; and a solvent in the amount of approximately 5%-30%.

10. A temperature therapy pack for providing hot and cold temperature therapy to a body part, and which displays color to indicate different therapy pack temperatures, comprising:

a visually transparent temperature therapy pack enclosure;

one or more thermochromic agents;

a pack fill material comprising one or more gels, said pack fill material being combined with said one or more thermochromic agents to collectively comprise a reversible thermochromic, thermal exchange material, said reversible thermochromic, thermal exchange material being enclosed in said visually transparent temperature therapy pack enclosure;

said reversible thermochromic, thermal exchange material being so compositionally, chemically configured such that it is capable of being alternately heated and cooled to provide heat or cold therapy, while remaining dimensionally stable;

said reversible thermochromic, thermal exchange material comprises a hydrogel formed into a plurality of structurally durable beads;

said temperature therapy pack being so configured such that when it is heated or cooled, said reversible thermochromic, thermal exchange material retains heat or cold, respectively, so that said temperature therapy pack can be applied to a body part of a user to provide hot or cold temperature therapy; and wherein said reversible thermochromic, thermal exchange material is so compositionally, chemically configured such as to:

display a first color within a temperature range T1 inclusive of room temperature;

display a second color within a temperature range T2, which is above said temperature range T1 and which is therapeutically suitable to provide heat therapy; and display a third color within a temperature range T3, which is below said temperature range T1 and which is therapeutically suitable to provide cold therapy;

wherein said one or more thermochromic agents comprise:

a first thermochromic agent; and a second thermochromic agent, wherein said first and said second thermochromic agents are particularly configured and selected such that when said thermal exchange material of said temperature therapy pack is measurable at a temperature within a temperature range T1, said temperature therapy pack displays a first color A; when said thermal exchange material of said temperature therapy pack is measurable at a temperature above said temperature range T1, said temperature therapy pack displays a second color B; and when said thermal exchange material of said temperature therapy pack is measurable at a temperature below said temperature range T1, said temperature therapy pack displays a third color C; and wherein one of said first, second, or third colors A, B, or C respectively is a color obtained through the spectral combination of the other two colors, such that three temperature therapy pack display colors are obtained utilizing only two thermochromic agents; and wherein said reversible thermochromic, thermal exchange material comprises, by mass fraction:

a polymer in the amount of approximately 5%-40%;

said first thermochromic agent in the amount of approximately 1%-3.5%;

said second thermochromic agent in the amount of approximately 1%-3.5%;

a dispersing agent in the amount of approximately 1.5%-33%;

a dispersing auxiliary in the amount of approximately 1.5%-35%;

a solvent in the amount of approximately 5%-30%; and wherein said polymer comprises at least one of a polyacrylic acid polymer, a natural polymer, and a cellulose derivative.

11. The temperature therapy pack according to claim 10 wherein said polymer comprises at least one of polyacrylic acid, sodium polyacrylate, polyacrylamide, and acrylamide/sodium acrylate copolymer, and wherein the raw materials for the polymerization of polyacrylic polymer comprise a monomer and an initiator; the monomer comprises one or more of acrylic acid and the relevant acrylate, acrylamide and acrylic ester; the initiator comprises one or more of potassium persulfate, ammonium persulfate, tert-butyl hydroperoxide and dimethyl sulfonyl peroxide; and the mass ratio of the monomer to initiator is about 50:1 to 200:1.

12. The temperature therapy pack according to claim 10 wherein said polymer comprises a natural polymer and said natural polymer is at least one selected from the group consisting of: agar, ammonium alginate, algin, alginic acid, amylopectin, gum tragacanth, calcium alginate, carrageenan, cassia gum, locust bean gum, quinoa starch, Guar gum, dehydroxanthan gum, dextrin, carrageenin, gelatin, Gellan gum, Ghatti gum, magnesium alginate, Natto gum, pectin, potassium alginate, potassium carrageenan, peach gum, Rhizobian gum, Sclerotium gum, sodium carrageenan, karaya gum, Tamarindus Indica seed gum, tapioca starch, TEA-alginate, Welan gum and Xathan gum.

13. The temperature therapy pack according to claim 10 wherein said polymer comprises a cellulose derivative and said cellulose derivative is at least one selected from the group consisting of: oxyhydroxypropyl cetyl hydroxyethylcellulose, calcium carboxymethyl cellulose, C12-16 alkyl PEG-2 hydroxypropyl hydroxyethyl ethylcellulose, carboxymethyl cellulose acetate butyrate, carboxymethyl hydroxyethyl cellulose, cellulase, cellulose acetate propionate, ascorbyl methylsilanol pectinate, calcium octenyl succinate starch, glyceryl alginate, hydrolyzed cellulose gum, hydroxyethyl chitosan, hydroxypropyl chitosan, hydroxypropyl guar gum, hydroxypropyl starch, hydroxypropyl starch phosphate, hydroxypropyl xanthan gum, carboxymethyl chitin, carboxymethyl chitosan, sodium carboxymethyl chitosan, sodium carboxymethyl dextrin, sodium polygluconate, sodium carboxymethyl starch, carboxymethyl glucosan, sodium starch octenyl succinate, starch hydroxypropyl trimethyl ammonium chloride, hexadecyl hydroxyethyl cellulose, croscarmellose, carboxymethyl hydroxypropyl guar gum, ethyl cellulose, sodium carboxymethyl cellulose, hydrogenated tallow benzyl dimethyl bentonite, hydroxybutyl methyl cellulose, hydroxyethyl cellulose, hydroxypropyl cellulose, hydroxypropyl methylcellulose, methyl cellulose, methyl ethyl cellulose, methyl hydroxyethyl cellulose, microcrystalline cellulose, nonylphenol polyether hydroxyethyl cellulose, oxycellulose, sodium cellulose sulfate and stearoxy PG-hydroxyethylcellulose sulfonate.

* * * * *